United States Patent
Mochly-Rosen

(10) Patent No.: US 7,994,133 B2
(45) Date of Patent: Aug. 9, 2011

(54) ISOZYME-SPECIFIC ANTAGONISTS OF PROTEIN KINASE C

(75) Inventor: Daria Mochly-Rosen, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 12/786,370

(22) Filed: May 24, 2010

(65) Prior Publication Data

US 2010/0311644 A1 Dec. 9, 2010

Related U.S. Application Data

(62) Division of application No. 12/283,921, filed on Sep. 15, 2008, now Pat. No. 7,745,412, which is a division of application No. 11/011,557, filed on Dec. 13, 2004, now abandoned.

(60) Provisional application No. 60/529,223, filed on Dec. 11, 2003.

(51) Int. Cl.
*A61K 38/08* (2006.01)
(52) U.S. Cl. ........................ 514/18.3; 514/21.7; 514/21.8
(58) Field of Classification Search ........................ None
See application file for complete search history.

(56) References Cited

U.S. PATENT DOCUMENTS

| | | | |
|---|---|---|---|
| 4,120,815 A | 10/1978 | Raman | |
| 4,457,371 A | 7/1984 | McCoy et al. | |
| 4,673,511 A | 6/1987 | Richardson et al. | |
| 4,699,951 A | 10/1987 | Allensen et al. | |
| 4,734,205 A | 3/1988 | Jacques et al. | |
| 5,128,046 A | 7/1992 | Marble et al. | |
| 5,783,405 A | 7/1998 | Mochly-Rosen et al. | |
| 6,042,732 A | 3/2000 | Jankowski et al. | |
| 6,165,977 A | 12/2000 | Mochly-Rosen | |
| 6,376,467 B1 * | 4/2002 | Messing et al. | 514/18.3 |
| 6,686,334 B2 * | 2/2004 | Messing et al. | 514/18.3 |
| 7,081,444 B2 | 7/2006 | Mochly-Rosen | |
| 7,459,424 B2 * | 12/2008 | Mochly-Rosen et al. | 514/1.1 |
| 7,544,654 B2 | 6/2009 | Mochly-Rosen | |

FOREIGN PATENT DOCUMENTS

| WO | WO 97/14038 A1 | 4/1997 |
|---|---|---|
| WO | WO 98/17299 | 4/1998 |
| WO | WO 98/21271 A1 | 5/1998 |
| WO | WO 02/078600 A2 | 10/2002 |

OTHER PUBLICATIONS

Aksoy, E. et al., "Protein kinase C epsilon: a new target to control inflammation and immune-mediated disorders", *International Journal of Biochemistry and Cell Biology*, 36:183-188 (2004).
Bogatkevich, G,S., et al., "Thrombin differentiates normal lung fibroblasts to a myofibroblast phenotype via the proteolytically activated receptor-1 and a protein kinase C-dependent pathway", *The Journal of Biological Chemistry*, 276(48):45184-45192 (2001).
Bradley, C.M. and Barrick, D., "Limits of cooperativity in a structurally modular protein: response of the Notch ankyrin domain to analogous alanine substitutions in each repeat", *Journal of Molecular Biology*, 324(2):373-386 (2002).
Chen et al. "Opposing cardioprotective actions and parallel hypertrophic effects of deltaa-PKC and epsilon-PKC," PNAS, 2001, 96, 11114-9.
Comalada, M. et al., "PKC epsilon is involved in JNK activation that mediates LPS-induced TNF-alpha, which induces apoptosis in macrophages", *Am. J. Physiol. Cell Physiol.*, 285:C1235-C1245 (2003).
Database UniProt Online!, "Transcription factor 12 (fragment)", retrieved from EBI accession No. UNIPROT: Q9NQY2, abstract (2000).
Disatnik, M.H. et al., "Sequential activation of individual PKC isozymes in integrin-mediated muscle cell spreading: a role for MARCKS in an integrin signaling pathway" *Journal of Cell Science*, 115(10):2151-2163 (2002).
Dorn II, G.W. et al., "Sustained in vivo cardiac protection by a rationally designed peptide that causes epsilon protein kinase C translocation", *Proc. Natl. Acad. Sci. USA*, 96(22):12798-12803 (1999).
Fang, Q. et al., "Thrombin induces collagen gel contraction partially through PAR1 activation and PKC-epsilon", *Eur. Respir. J.*, 24:918-924 (2004).
Flanagan, J.M. et al., "Truncated staphylococcal nuclease is compact but disordered", *Proc. Natl. Acad. Sci. USA*, 89(2):748-752 (1992).
Ginalski, K. et al., "Practical lessons from protein structure prediction", *Nucleic Acid Research*, 33(6):1874-1891 (2005).
Johnson, J.A., et al., "A protein kinase C translocation inhibitor as an isozyme-selective antagonist of cardiac function", *The Journal of Biological Chemistry*, 271(40):24962-24966 (1996).
Pitt, M. et al., "Single amino acid substitution mutants of *Klebsiella pneumoniae* sigma(54) defective in transcription", *Nucleic Acid Research*, 28(22):4419-4427 (2000).
Ron, D. and Mochly-Rosen, D., "An autoregulatory region in protein kinase C: the pseudoanchoring site", *Proc. Natl. Acad. Sci. USA*, 92(2):492-496 (1995).
Ron, D., et al., "C2 region-derived peptides inhibit translocation and function of beta protein kinase C in vivo", *The Journal of Biological Chemistry*, 270(41):24180-24187 (1995).

(Continued)

*Primary Examiner* — Christina Bradley
(74) *Attorney, Agent, or Firm* — Judy M. Mohr; Susan L. Harlocker; King & Spalding LLP

(57) ABSTRACT

A method of changing or otherwise converting the biological activity of a PKC peptide agonist to a peptide antagonist is described. The method involves substituting one or more amino acid residues so as to effect a change in charge in the peptide and/or to otherwise make the sequence similar to a sequence derived from the PKC binding site on the RACK protein for the respective PKC enzyme. Methods of inhibiting the activity of a PKC enzyme, and various peptide antagonists of εPKC are also disclosed.

16 Claims, 14 Drawing Sheets

OTHER PUBLICATIONS

Ron et al., "Agonists and Antagonists of Protein Kinase C Function, Derived from its Binding Proteins" *Journal of Biological Chemistry*, 269(34):21395-21398 (1994).

Rudinger, "Characteristic of the amino acids as components of a peptide hormone sequence", (Peptide Hormones (Ed. J.A. Parson) University Park Press. Baltimore pp. 1-7 (1976).

Sawai, M.V. et al., "Impact of single-residue mutations on the structure and function of ovispirin/novispirin antimicrobial peptides", *Prot. Engin.*, 15(3):225-232 (2002).

Schechtman, D. et al., "A critical intramolecular interaction for protein kinase Cepsilon translocation", *The Journal of Biological Chemistry*, 279(16):15831-15840 (2004).

Schnog, J.B. et al., "Sickle cell disease; a general overview", *J. Med.* 62:364-374 (2004).

Souroujon M C et al., "Peptide Modulators of Protein-Protein Interactions in Intracellularsignaling" *Nature Biotechnology, Nature Publishing*, 16(10):919 (1998).

Wadia & Dowdy "Protein transduction technology," Curr Opin Biotech, 2002, 13,52-56.

Liron, et al., "Rational design of a selective antagonist of epsilon protein kinase C derived from the selective allosteric agonist, pseudo-RACK peptide", J. Mol. Cell. Cardiol., vol. 42, No. 4, p. 835-841 (2007).

* cited by examiner

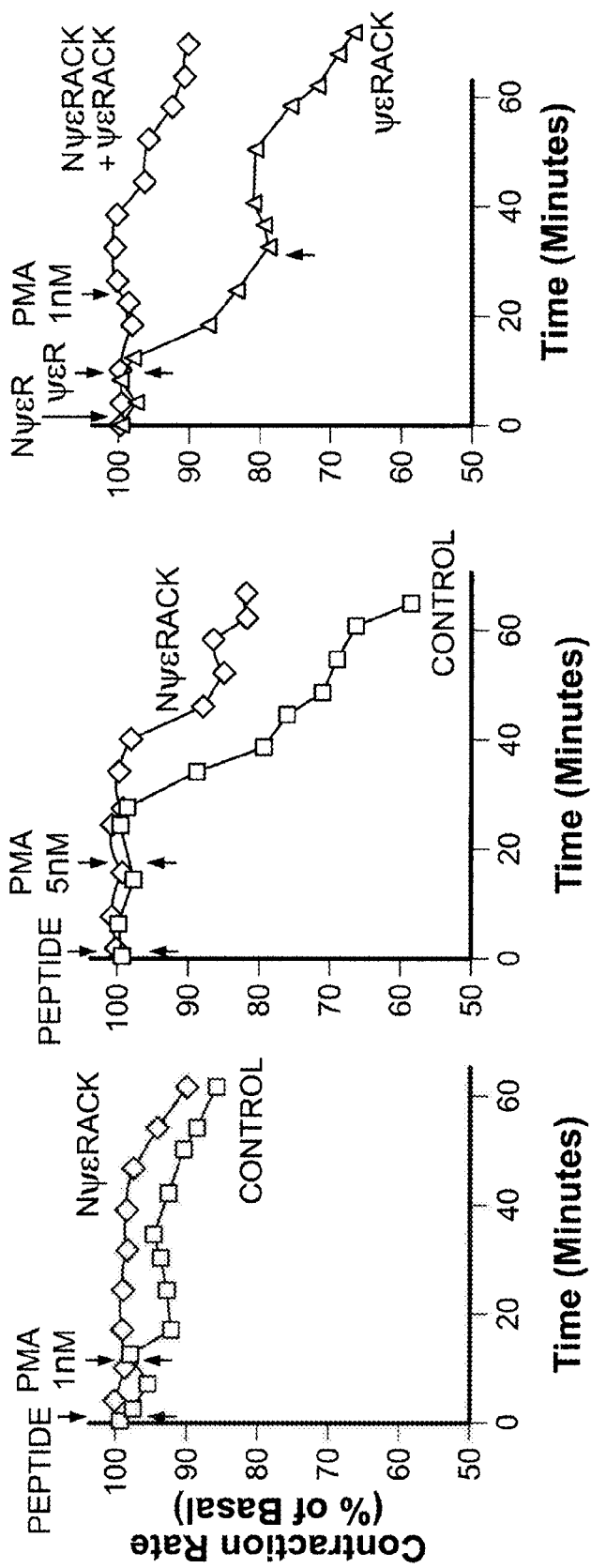

SEQUENCE LISTING

```
<160> NUMBER OF SEQ ID NOS: 97

<210> SEQ ID NO 1
<211> LENGTH: 8
<212> TYPE: PRT
<213> ORGANISM: Homo sapiens

<400> SEQUENCE: 1

Asn Asn Val Ala Leu Gly Tyr Asp
1               5

<210> SEQ ID NO 2
<211> LENGTH: 6
<212> TYPE: PRT
<213> ORGANISM: Homo sapiens

<400> SEQUENCE: 2

Ser Ile Lys Ile Trp Asp
1               5

<210> SEQ ID NO 3
<211> LENGTH: 8
<212> TYPE: PRT
<213> ORGANISM: Homo sapiens

<400> SEQUENCE: 3

His Asp Ala Pro Ile Gly Tyr Asp
1               5

<210> SEQ ID NO 4
<211> LENGTH: 8
<212> TYPE: PRT
<213> ORGANISM: Homo sapiens

<400> SEQUENCE: 4

Met Arg Ala Ala Glu Glu Pro Met
1               5

<210> SEQ ID NO 5
<211> LENGTH: 8
<212> TYPE: PRT
<213> ORGANISM: Homo sapiens

<400> SEQUENCE: 5

Lys Gly Lys Asn Val Asp Leu Ile
1               5

<210> SEQ ID NO 6
<211> LENGTH: 8
<212> TYPE: PRT
<213> ORGANISM: Homo sapiens

<400> SEQUENCE: 6

His Glu Thr Pro Leu Gly Tyr Asp
1               5

<210> SEQ ID NO 7
<211> LENGTH: 6
<212> TYPE: PRT
```

```
<213> ORGANISM: Homo sapiens

<400> SEQUENCE: 7

Ser Val Glu Ile Trp Asp
1               5

<210> SEQ ID NO 8
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 8

His Glu Ala Asp Ile Gly Tyr Asp
1               5

<210> SEQ ID NO 9
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 9

His Asp Ala Pro Ile Gly Tyr Glu
1               5

<210> SEQ ID NO 10
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 10

His Asp Ala Pro Val Gly Tyr Glu
1               5

<210> SEQ ID NO 11
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 11

His Asp Ala Pro Leu Gly Tyr Glu
1               5

<210> SEQ ID NO 12
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 12

His Asp Ala Pro Ile Gly Asp Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: Alternative pseudo-epsilon RACK peptide
```

```
<400> SEQUENCE: 13

His Asp Ala Pro Ile Gly Glu Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 14

Ala Asp Ala Pro Ile Gly Tyr Asp
1               5

<210> SEQ ID NO 15
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 15

His Asp Gly Pro Ile Gly Tyr Asp
1               5

<210> SEQ ID NO 16
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 16

His Asp Ala Ala Ile Gly Tyr Asp
1               5

<210> SEQ ID NO 17
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 17

Ala Glu Ala Pro Val Gly Glu Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 18

His Glu Ala Pro Ile Gly Asp Asn
1               5

<210> SEQ ID NO 19
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 19
```

```
His Asp Gly Asp Ile Gly Tyr Asp
1               5

<210> SEQ ID NO 20
<211> LENGTH: 6
<212> TYPE: PRT
<213> ORGANISM: Artificial Sequence
<220> FEATURE:
<223> OTHER INFORMATION: Alternative pseudo-epsilon RACK peptide

<400> SEQUENCE: 20

His Asp Ala Pro Ile Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 21

His Asp Ala Pro Ile Pro Tyr Asp
1               5

<210> SEQ ID NO 22
<211> LENGTH: 8
<212> TYPE: PRT
<213> ORGANISM: Artificial Sequence
<220> FEATURE:
<223> OTHER INFORMATION: Alternative pseudo-delta RACK peptide

<400> SEQUENCE: 22

Met Arg Val Ala Glu Glu Pro Val
1               5

<210> SEQ ID NO 23
<211> LENGTH: 8
<212> TYPE: PRT
<213> ORGANISM: Artificial Sequence
<220> FEATURE:
<223> OTHER INFORMATION: Alternative pseudo-delta RACK peptide

<400> SEQUENCE: 23

Met Arg Val Val Glu Glu Pro Val
1               5

<210> SEQ ID NO 24
<211> LENGTH: 8
<212> TYPE: PRT
<213> ORGANISM: Artificial Sequence
<220> FEATURE:
<223> OTHER INFORMATION: Alternative pseudo-delta RACK peptide

<400> SEQUENCE: 24

Met Arg Ala Ala Asp Glu Pro Val
1               5

<210> SEQ ID NO 25
<211> LENGTH: 7
<212> TYPE: PRT
<213> ORGANISM: Artificial Sequence
<220> FEATURE:
<223> OTHER INFORMATION: Alternative pseudo-delta RACK peptide

<400> SEQUENCE: 25

Met Arg Ala Ala Glu Glu Pro
1               5
```

```
<210> SEQ ID NO 26
<211> LENGTH: 8
<212> TYPE: PRT
<213> ORGANISM: Artificial Sequence
<220> FEATURE:
<223> OTHER INFORMATION: Alternative pseudo-delta RACK peptide

<400> SEQUENCE: 26

Met Arg Leu Leu Glu Glu Pro Val
1               5

<210> SEQ ID NO 27
<211> LENGTH: 8
<212> TYPE: PRT
<213> ORGANISM: Artificial Sequence
<220> FEATURE:
<223> OTHER INFORMATION: Alternative pseudo-delta RACK peptide

<400> SEQUENCE: 27

Met Arg Leu Ala Glu Glu Pro Val
1               5

<210> SEQ ID NO 28
<211> LENGTH: 6
<212> TYPE: PRT
<213> ORGANISM: Artificial Sequence
<220> FEATURE:
<223> OTHER INFORMATION: Alternative pseudo-delta RACK peptide

<400> SEQUENCE: 28

Met Arg Ala Ala Glu Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Alternative pseudo-eta RACK peptide

<400> SEQUENCE: 29

His Asp Thr Pro Leu Gly Tyr Asp
1               5

<210> SEQ ID NO 30
<211> LENGTH: 6
<212> TYPE: PRT
<213> ORGANISM: Artificial Sequence
<220> FEATURE:
<223> OTHER INFORMATION: Alternative pseudo-eta RACK peptide

<400> SEQUENCE: 30

His Asp Thr Pro Leu Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Alternative pseudo-eta RACK peptide

<400> SEQUENCE: 31

His Asp Thr Pro Ile Gly Tyr Asp
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: Alternative pseudo-eta RACK peptide

<400> SEQUENCE: 32

His Glu Thr Pro Ala Gly Tyr Asp
1               5

<210> SEQ ID NO 33
<211> LENGTH: 8
<212> TYPE: PRT
<213> ORGANISM: Artificial Sequence
<220> FEATURE:
<223> OTHER INFORMATION: Alternative pseudo-eta RACK peptide

<400> SEQUENCE: 33

His Glu Thr Pro Ala Gly Tyr Glu
1               5

<210> SEQ ID NO 34
<211> LENGTH: 8
<212> TYPE: PRT
<213> ORGANISM: Artificial Sequence
<220> FEATURE:
<223> OTHER INFORMATION: Alternative pseudo-eta RACK peptide

<400> SEQUENCE: 34

Lys Glu Thr Pro Ala Gly Tyr Asp
1               5

<210> SEQ ID NO 35
<211> LENGTH: 8
<212> TYPE: PRT
<213> ORGANISM: Artificial Sequence
<220> FEATURE:
<223> OTHER INFORMATION: Alternative pseudo-eta RACK peptide

<400> SEQUENCE: 35

Lys Glu Thr Pro Val Gly Tyr Asp
1               5

<210> SEQ ID NO 36
<211> LENGTH: 6
<212> TYPE: PRT
<213> ORGANISM: Artificial Sequence
<220> FEATURE:
<223> OTHER INFORMATION: Alternative pseudo-eta RACK peptide

<400> SEQUENCE: 36

Lys Glu Thr Pro Val Gly
1               5

<210> SEQ ID NO 37
<211> LENGTH: 8
<212> TYPE: PRT
<213> ORGANISM: Artificial Sequence
<220> FEATURE:
<223> OTHER INFORMATION: Alternative pseudo-theta RACK peptide

<400> SEQUENCE: 37

Arg Gly Lys Asn Val Glu Leu Ala
1               5

<210> SEQ ID NO 38
<211> LENGTH: 6
```

```
<212> TYPE: PRT
<213> ORGANISM: Artificial Sequence
<220> FEATURE:
<223> OTHER INFORMATION: Alternative pseudo-theta RACK peptide

<400> SEQUENCE: 38

Lys Asn Val Asp Leu Ile
1               5

<210> SEQ ID NO 39
<211> LENGTH: 8
<212> TYPE: PRT
<213> ORGANISM: Artificial Sequence
<220> FEATURE:
<223> OTHER INFORMATION: Alternative pseudo-theta RACK peptide

<400> SEQUENCE: 39

Arg Gly Arg Asn Val Asp Leu Ile
1               5

<210> SEQ ID NO 40
<211> LENGTH: 8
<212> TYPE: PRT
<213> ORGANISM: Artificial Sequence
<220> FEATURE:
<223> OTHER INFORMATION: Alternative pseudo-theta RACK peptide

<400> SEQUENCE: 40

Lys Gly Arg Asn Ala Asp Leu Ile
1               5

<210> SEQ ID NO 41
<211> LENGTH: 8
<212> TYPE: PRT
<213> ORGANISM: Artificial Sequence
<220> FEATURE:
<223> OTHER INFORMATION: Alternative pseudo-theta RACK peptide

<400> SEQUENCE: 41

Lys Gly Lys Asn Val Glu Leu Ile
1               5

<210> SEQ ID NO 42
<211> LENGTH: 8
<212> TYPE: PRT
<213> ORGANISM: Artificial Sequence
<220> FEATURE:
<223> OTHER INFORMATION: Alternative pseudo-theta RACK peptide

<400> SEQUENCE: 42

Lys Gly Lys Asn Val Glu Leu Ala
1               5

<210> SEQ ID NO 43
<211> LENGTH: 8
<212> TYPE: PRT
<213> ORGANISM: Artificial Sequence
<220> FEATURE:
<223> OTHER INFORMATION: Alternative pseudo-theta RACK peptide

<400> SEQUENCE: 43

Lys Gly Lys Gln Val Asp Leu Ile
1               5

<210> SEQ ID NO 44
<211> LENGTH: 8
<212> TYPE: PRT
<213> ORGANISM: Artificial Sequence
```

```
<220> FEATURE:
<223> OTHER INFORMATION: Alternative pseudo-theta RACK peptide

<400> SEQUENCE: 44

Arg Gly Lys Asn Leu Asp Leu Ile
1               5

<210> SEQ ID NO 45
<211> LENGTH: 6
<212> TYPE: PRT
<213> ORGANISM: Artificial Sequence
<220> FEATURE:
<223> OTHER INFORMATION: Alternative pseudo-beta RACK peptide

<400> SEQUENCE: 45

Ser Ala Glu Ile Trp Asp
1               5

<210> SEQ ID NO 46
<211> LENGTH: 6
<212> TYPE: PRT
<213> ORGANISM: Artificial Sequence
<220> FEATURE:
<223> OTHER INFORMATION: Alternative pseudo-beta RACK peptide

<400> SEQUENCE: 46

Ser Val Glu Leu Trp Asp
1               5

<210> SEQ ID NO 47
<211> LENGTH: 6
<212> TYPE: PRT
<213> ORGANISM: Artificial Sequence
<220> FEATURE:
<223> OTHER INFORMATION: Alternative pseudo-beta RACK peptide

<400> SEQUENCE: 47

Thr Val Glu Ile Trp Asp
1               5

<210> SEQ ID NO 48
<211> LENGTH: 6
<212> TYPE: PRT
<213> ORGANISM: Artificial Sequence
<220> FEATURE:
<223> OTHER INFORMATION: Alternative pseudo-beta RACK peptide

<400> SEQUENCE: 48

Ser Val Glu Ile Trp Glu
1               5

<210> SEQ ID NO 49
<211> LENGTH: 5
<212> TYPE: PRT
<213> ORGANISM: Artificial Sequence
<220> FEATURE:
<223> OTHER INFORMATION: Alternative pseudo-beta RACK peptide

<400> SEQUENCE: 49

Ser Val Glu Ile Trp
1               5

<210> SEQ ID NO 50
<211> LENGTH: 8
<212> TYPE: PRT
<213> ORGANISM: Artificial Sequence
<220> FEATURE:
<223> OTHER INFORMATION: A modification of SEQ ID NO:3
```

```
<400> SEQUENCE: 50

His Asn Ala Pro Ile Gly Asp Tyr
1               5

<210> SEQ ID NO 51
<211> LENGTH: 8
<212> TYPE: PRT
<213> ORGANISM: Artificial Sequence
<220> FEATURE:
<223> OTHER INFORMATION: A modification of SEQ ID NO:3

<400> SEQUENCE: 51

His Asp Ala Pro Ile Gly Asn Tyr
1               5

<210> SEQ ID NO 52
<211> LENGTH: 6
<212> TYPE: PRT
<213> ORGANISM: Artificial Sequence
<220> FEATURE:
<223> OTHER INFORMATION: A modification of SEQ ID NO:3

<400> SEQUENCE: 52

His Asn Ala Pro Ile Gly
1               5

<210> SEQ ID NO 53
<211> LENGTH: 8
<212> TYPE: PRT
<213> ORGANISM: Artificial Sequence
<220> FEATURE:
<223> OTHER INFORMATION: A modification of SEQ ID NO:3

<400> SEQUENCE: 53

His Asn Ala Pro Ile Pro Tyr Asp
1               5

<210> SEQ ID NO 54
<211> LENGTH: 8
<212> TYPE: PRT
<213> ORGANISM: Artificial Sequence
<220> FEATURE:
<223> OTHER INFORMATION: A modification of SEQ ID NO:3

<400> SEQUENCE: 54

His Asp Ala Pro Ile Pro Tyr Asn
1               5

<210> SEQ ID NO 55
<211> LENGTH: 8
<212> TYPE: PRT
<213> ORGANISM: Artificial Sequence
<220> FEATURE:
<223> OTHER INFORMATION: A modification of SEQ ID NO:3

<400> SEQUENCE: 55

His Asn Ala Pro Ile Gly Tyr Asp
1               5

<210> SEQ ID NO 56
<211> LENGTH: 8
<212> TYPE: PRT
<213> ORGANISM: Artificial Sequence
<220> FEATURE:
<223> OTHER INFORMATION: A modification of SEQ ID NO:3

<400> SEQUENCE: 56
```

```
His Asn Ala Ala Ile Gly Tyr Asp
1               5

<210> SEQ ID NO 57
<211> LENGTH: 8
<212> TYPE: PRT
<213> ORGANISM: Artificial Sequence
<220> FEATURE:
<223> OTHER INFORMATION: A modification of SEQ ID NO:3

<400> SEQUENCE: 57

His Asp Ala Ala Ile Gly Tyr Asn
1               5

<210> SEQ ID NO 58
<211> LENGTH: 8
<212> TYPE: PRT
<213> ORGANISM: Artificial Sequence
<220> FEATURE:
<223> OTHER INFORMATION: A modification of SEQ ID NO:4

<400> SEQUENCE: 58

Met Asp Val Ala Glu Glu Pro Val
1               5

<210> SEQ ID NO 59
<211> LENGTH: 8
<212> TYPE: PRT
<213> ORGANISM: Artificial Sequence
<220> FEATURE:
<223> OTHER INFORMATION: A modification of SEQ ID NO:4

<400> SEQUENCE: 59

Met Glu Val Ala Glu Glu Pro Val
1               5

<210> SEQ ID NO 60
<211> LENGTH: 8
<212> TYPE: PRT
<213> ORGANISM: Artificial Sequence
<220> FEATURE:
<223> OTHER INFORMATION: A modification of SEQ ID NO:4

<400> SEQUENCE: 60

Met Arg Val Ala Glu Asn Pro Val
1               5

<210> SEQ ID NO 61
<211> LENGTH: 8
<212> TYPE: PRT
<213> ORGANISM: Artificial Sequence
<220> FEATURE:
<223> OTHER INFORMATION: A modification of SEQ ID NO:4

<400> SEQUENCE: 61

Met Arg Val Ala Glu Gln Pro Val
1               5

<210> SEQ ID NO 62
<211> LENGTH: 8
<212> TYPE: PRT
<213> ORGANISM: Artificial Sequence
<220> FEATURE:
<223> OTHER INFORMATION: A modification of SEQ ID NO:4

<400> SEQUENCE: 62

Met Asp Leu Ala Glu Glu Pro Val
```

```
<210> SEQ ID NO 63
<211> LENGTH: 8
<212> TYPE: PRT
<213> ORGANISM: Artificial Sequence
<220> FEATURE:
<223> OTHER INFORMATION: A modification of SEQ ID NO:4

<400> SEQUENCE: 63

Met Glu Leu Ala Glu Glu Pro Val
1               5

<210> SEQ ID NO 64
<211> LENGTH: 8
<212> TYPE: PRT
<213> ORGANISM: Artificial Sequence
<220> FEATURE:
<223> OTHER INFORMATION: A modification of SEQ ID NO:4

<400> SEQUENCE: 64

Met Arg Leu Ala Glu Asn Pro Val
1               5

<210> SEQ ID NO 65
<211> LENGTH: 8
<212> TYPE: PRT
<213> ORGANISM: Artificial Sequence
<220> FEATURE:
<223> OTHER INFORMATION: A modification of SEQ ID NO:4

<400> SEQUENCE: 65

Met Arg Leu Ala Glu Gln Pro Val
1               5

<210> SEQ ID NO 66
<211> LENGTH: 8
<212> TYPE: PRT
<213> ORGANISM: Artificial Sequence
<220> FEATURE:
<223> OTHER INFORMATION: A modification of SEQ ID NO:6

<400> SEQUENCE: 66

His Gln Thr Pro Leu Gly Tyr Asp
1               5

<210> SEQ ID NO 67
<211> LENGTH: 8
<212> TYPE: PRT
<213> ORGANISM: Artificial Sequence
<220> FEATURE:
<223> OTHER INFORMATION: A modification of SEQ ID NO:6

<400> SEQUENCE: 67

His Asn Thr Pro Leu Gly Tyr Asp
1               5

<210> SEQ ID NO 68
<211> LENGTH: 8
<212> TYPE: PRT
<213> ORGANISM: Artificial Sequence
<220> FEATURE:
<223> OTHER INFORMATION: A modification of SEQ ID NO:6

<400> SEQUENCE: 68

Lys Gln Thr Pro Ala Gly Tyr Asp
1               5
```

```
<210> SEQ ID NO 69
<211> LENGTH: 8
<212> TYPE: PRT
<213> ORGANISM: Artificial Sequence
<220> FEATURE:
<223> OTHER INFORMATION: A modification of SEQ ID NO:6

<400> SEQUENCE: 69

Lys Asn Thr Pro Ala Gly Tyr Asp
1               5

<210> SEQ ID NO 70
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 70

Lys Gly Asp Asn Val Asp Leu Ile
1               5

<210> SEQ ID NO 71
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 71

Lys Gly Glu Asn Val Asp Leu Ile
1               5

<210> SEQ ID NO 72
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 72

Lys Gly Lys Glu Val Asp Leu Ile
1               5

<210> SEQ ID NO 73
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 73

Lys Gly Lys Asn Val Asn Leu Ile
1               5

<210> SEQ ID NO 74
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 74

Arg Gly Asp Asn Val Glu Leu Ala
1               5

<210> SEQ ID NO 75
```

```
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 75

Arg Gly Glu Asn Val Glu Leu Ala
1               5

<210> SEQ ID NO 76
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 76

Lys Gly Lys Gln Val Asn Leu Ile
1               5

<210> SEQ ID NO 77
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 77

Lys Gly Asp Gln Val Asn Leu Ile
1               5

<210> SEQ ID NO 78
<211> LENGTH: 8
<212> TYPE: PRT
<213> ORGANISM: Artificial Sequence
<220> FEATURE:
<223> OTHER INFORMATION: A modification of SEQ ID NO:5

<400> SEQUENCE: 78

Lys Gly Glu Gln Val Asn Leu Ile
1               5

<210> SEQ ID NO 79
<211> LENGTH: 8
<212> TYPE: PRT
<213> ORGANISM: Artificial Sequence
<220> FEATURE:
<223> OTHER INFORMATION: Alternative pseudo-epsilon RACK peptide

<400> SEQUENCE: 79

His Ala Ala Pro Ile Gly Tyr Asp
1               5

<210> SEQ ID NO 80
<211> LENGTH: 6
<212> TYPE: PRT
<213> ORGANISM: Artificial Sequence
<220> FEATURE:
<223> OTHER INFORMATION: A modification of SEQ ID NO:7

<400> SEQUENCE: 80

Ser Val Lys Ile Trp Asp
1               5

<210> SEQ ID NO 81
<211> LENGTH: 6
<212> TYPE: PRT
```

```
<213> ORGANISM: Artificial Sequence
<220> FEATURE:
<223> OTHER INFORMATION: A modification of SEQ ID NO:7

<400> SEQUENCE: 81

Ser Ala Lys Ile Trp Asp
1               5

<210> SEQ ID NO 82
<211> LENGTH: 6
<212> TYPE: PRT
<213> ORGANISM: Artificial Sequence
<220> FEATURE:
<223> OTHER INFORMATION: A modification of SEQ ID NO:7

<400> SEQUENCE: 82

Ser Val Lys Leu Trp Asp
1               5

<210> SEQ ID NO 83
<211> LENGTH: 6
<212> TYPE: PRT
<213> ORGANISM: Artificial Sequence
<220> FEATURE:
<223> OTHER INFORMATION: A modification of SEQ ID NO:7

<400> SEQUENCE: 83

Thr Val Lys Ile Trp Glu
1               5

<210> SEQ ID NO 84
<211> LENGTH: 6
<212> TYPE: PRT
<213> ORGANISM: Artificial Sequence
<220> FEATURE:
<223> OTHER INFORMATION: A modification of SEQ ID NO:7

<400> SEQUENCE: 84

Ser Val Lys Ile Trp Glu
1               5

<210> SEQ ID NO 85
<211> LENGTH: 5
<212> TYPE: PRT
<213> ORGANISM: Artificial Sequence
<220> FEATURE:
<223> OTHER INFORMATION: A modification of SEQ ID NO:7

<400> SEQUENCE: 85

Ser Val Lys Ile Trp
1               5

<210> SEQ ID NO 86
<211> LENGTH: 8
<212> TYPE: PRT
<213> ORGANISM: Homo sapiens

<400> SEQUENCE: 86

Glu Ala Val Ser Leu Lys Pro Thr
1               5

<210> SEQ ID NO 87
<211> LENGTH: 33
<212> TYPE: DNA
<213> ORGANISM: Artificial Sequence
<220> FEATURE:
<223> OTHER INFORMATION: Primer used for site-directed mutagenesis to
      form D(86)N mutant in Example 4
```

```
<400> SEQUENCE: 87
gtagcctatg ggggcattgt gaaagacagc cag                                33

<210> SEQ ID NO 88
<211> LENGTH: 33
<212> TYPE: PRT
<213> ORGANISM: Artificial Sequence
<220> FEATURE:
<223> OTHER INFORMATION: Complementary strand of SEQ ID NO:87

<400> SEQUENCE: 88

Cys Thr Gly Gly Cys Thr Gly Thr Cys Thr Thr Thr Cys Ala Cys Ala
1               5                   10                  15

Ala Thr Gly Cys Cys Cys Cys Ala Thr Ala Gly Gly Cys Thr Ala
            20                  25                  30

Cys

<210> SEQ ID NO 89
<211> LENGTH: 33
<212> TYPE: DNA
<213> ORGANISM: Artificial Sequence
<220> FEATURE:
<223> OTHER INFORMATION: Primer used for site-directed mutagenesis to
      form D(86)A mutant in Example 4

<400> SEQUENCE: 89
ctggctgtct ttcacgctgc ccccataggc tac                                33

<210> SEQ ID NO 90
<211> LENGTH: 33
<212> TYPE: DNA
<213> ORGANISM: Artificial Sequence
<220> FEATURE:
<223> OTHER INFORMATION: Complementary strand of SEQ ID NO:89

<400> SEQUENCE: 90
gtagcctatg ggggcagcgt gaaagacagc cag                                33

<210> SEQ ID NO 91
<211> LENGTH: 17
<212> TYPE: PRT
<213> ORGANISM: Artificial Sequence
<220> FEATURE:
<223> OTHER INFORMATION: Drosophila Antennapedia homeodomain-derived
      carrier peptide

<400> SEQUENCE: 91

Cys Arg Gln Ile Lys Ile Trp Phe Gln Asn Arg Arg Met Lys Trp Lys
1               5                   10                  15

Lys

<210> SEQ ID NO 92
<211> LENGTH: 11
<212> TYPE: PRT
<213> ORGANISM: Artificial Sequence
<220> FEATURE:
<223> OTHER INFORMATION: HIV type 1 Tat-derived carrier peptide

<400> SEQUENCE: 92

Tyr Gly Arg Lys Lys Arg Arg Gln Arg Arg Arg
1               5                   10

<210> SEQ ID NO 93
<211> LENGTH: 30
```

```
<212> TYPE: PRT
<213> ORGANISM: Homo sapiens

<400> SEQUENCE: 93

Thr Asp Val Cys Asn Gly Arg Lys Ile Glu Leu Ala Val Phe His Asp
1               5                   10                  15

Ala Pro Ile Gly Tyr Asp Asp Phe Val Ala Asn Cys Thr Ile
            20                  25                  30

<210> SEQ ID NO 94
<211> LENGTH: 18
<212> TYPE: PRT
<213> ORGANISM: Homo sapiens

<400> SEQUENCE: 94

Ile Gln Ile Val Leu Met Arg Ala Ala Glu Glu Pro Val Ser Glu Val
1               5                   10                  15

Thr Val

<210> SEQ ID NO 95
<211> LENGTH: 18
<212> TYPE: PRT
<213> ORGANISM: Homo sapiens

<400> SEQUENCE: 95

Met Gln Ile Ile Val Lys Gly Lys Asn Val Asp Leu Ile Ser Glu Thr
1               5                   10                  15

Thr Val

<210> SEQ ID NO 96
<211> LENGTH: 18
<212> TYPE: PRT
<213> ORGANISM: Homo sapiens

<400> SEQUENCE: 96

Glu Leu Ala Val Phe His Glu Thr Pro Leu Gly Tyr Asp His Phe Val
1               5                   10                  15

Ala Asn

<210> SEQ ID NO 97
<211> LENGTH: 16
<212> TYPE: PRT
<213> ORGANISM: Homo sapiens

<400> SEQUENCE: 97

Lys Asp Arg Arg Leu Ser Val Glu Ile Trp Asp Trp Asp Trp Asp Leu
1               5                   10                  15
```

ISOZYME-SPECIFIC ANTAGONISTS OF PROTEIN KINASE C

CROSS-REFERENCE TO RELATED APPLICATIONS

This application is a Divisional application of U.S. patent application Ser. No. 12/283,921, filed Sep. 15, 2008 now U.S. Pat. No. 7,745,412, now allowed, which is a Divisional application of U.S. patent application Ser. No. 11/011,557, filed Dec. 13, 2004, now abandoned, which claims the benefit of U.S. Provisional Patent Application Ser. No. 60/529,223, filed Dec. 11, 2003, each of which are hereby incorporated by reference in their entirety.

STATEMENT REGARDING GOVERNMENT INTEREST

This invention was made with Government support under contract HL052141awarded by the National Institutes of Health. The Government has certain rights in this invention.

REFERENCE TO SEQUENCE LISTING, TABLE OR COMPUTER PROGRAM

A "Sequence Listing" is submitted with this application in the form of a text file, created 10 May 2010, and named "586008212US02seqlist.txt" (20480 bytes on disk), the content of which are incorporated herein by reference in their entirety.

FIELD OF THE INVENTION

The present invention relates to a method of converting the biological action of an agonist to an antagonist, and in particular a method of converting an agonist of protein kinase C to an antagonist of protein kinase C. The present invention also relates to a peptide composition for isozyme-specific modulation of protein kinase C and to a method of antagonizing the action of specific isozymes of protein kinase C.

BACKGROUND OF THE INVENTION

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, $\alpha$, $\beta_I$, $\beta_{II}$ and $\gamma$PKC, contain four homologous domains (C1, C2, C3 and C4) and require calcium, phosphatidylserine, and diacylglycerol or phorbol esters for activation. In members of the "novel" or "nPKC" subfamily, $\delta$, $\epsilon$, $\eta$ and $\theta$PKC, a C2-like domain precedes the C1 domain. However, that C2 domain does not bind calcium and therefore the nPKC subfamily does not require calcium for activation. Finally, members of the "atypical" or "aPKC" subfamily, $\zeta$ and $\lambda/\iota$PKC, lack both the C2 and one-half of the C1 homologous domains and are insensitive to diacylglycerol, phorbol esters and calcium.

Studies on the subcellular distribution of PKC isozymes demonstrate that activation of PKC results in its redistribution in the cells (also termed translocation), such that activated PKC isozymes associate with the plasma membrane, cytoskeletal elements, nuclei, and other subcellular compartments (Saito, N. et al., *Proc. Natl. Acad. Sci. USA* 86:3409-3413 (1989); Papadopoulos, V. and Hall, P. F. *J. Cell Biol.* 108:553-567 (1989); Mochly-Rosen, D., et al., *Molec. Biol. Cell* (formerly *Cell Reg.*) 1:693-706, (1990)). The unique cellular functions of different PKC isozymes are determined by their subcellular location. For example, activated $\beta_I$PKC is found inside the nucleus, whereas activated $\beta_{II}$PKC is found at the perinucleus and cell periphery of cardiac myocytes (Disatnik, M. H., et al., *Exp. Cell Res.* 210:287-297 (1994)). $\epsilon$PKC, a member of the novel PKC family independent from calcium but requiring phospholipids for activation, is found in primary afferent neurons both in the dorsal root ganglia as well as in the superficial layers of the dorsal spinal cord.

The localization of different PKC isozymes to different areas of the cell in turn appears due to binding of the activated isozymes to specific anchoring molecules termed Receptors for Activated C-Kinase ("RACKs"). RACKs are thought to function by selectively anchoring activated PKC isozymes to their respective subcellular sites. RACKs bind only fully activated PKC and are not necessarily substrates of the enzyme. Nor is the binding to RACKs mediated via the catalytic domain of the kinase (Mochly-Rosen, D., et al., *Proc. Natl. Acad. Sci. USA* 88:3997-4000 (1991)). Translocation of PKC reflects binding of the activated enzyme to RACKs and the binding to RACKs is required for PKC to produce its cellular responses (Mochly-Rosen, D., et al., *Science* 268:247-251 (1995)). Inhibition of PKC binding to RACKs in vivo inhibits PKC translocation and PKC-mediated function (Johnson, J. A., et al., *J. Biol. Chem.* 271:24962-24966 (1996); Ron, D., et al., *Proc. Natl. Acad. Sci. USA* 92:492-496 (1995); Smith, B. L. and Mochly-Rosen, D., *Biochem. Biophys. Res. Commun.* 188:1235-1240 (1992)).

In general, translocation of PKC is required for proper function of PKC isozymes. Peptides that mimic the RACK-binding site on PKC [Ron, D., et al., *Proc. Natl. Acad. Sci. USA* 92:492-496 (1995); Johnson, J. A., et al., *J. Biol. Chem.* 271:24962-24966 (1996)] are isozyme-specific translocation inhibitors of PKC that selectively inhibit the function of the enzyme in vivo. Such isozyme-selective inhibitors of PKC have been identified based on their ability to selectively inhibit the interaction of the activated isozymes with their respective anchoring proteins (RACKs) (Souroujon, M. and Mochly-Rosen, D., *Nature Biotechnol.* 16:919-924, (1998)). These short peptide inhibitors (7-12 amino acids long) have been shown to selectively interfere with the functions of individual isozymes (Mochly-Rosen, D., et al., *Proc. Natl. Acad. Sci. USA* 88:3997-4000, (1991); Ron, D., et al., *J. Biol. Chem.* 270:24180-24187, (1995); Johnson, J. A., et at, *J. Biol. Chem.* 271:24962-24966, (1996); Zhang, Z., et al., *Biophys. J.* 70(2, part 2):A391, (1996); Gray, M. O., et al., *J. Biol. Chem.* 272:30945-30951, (1997)).

Translocation agonist peptides of $\beta$ and $\epsilon$PKC, as well as other PKC isozymes, have also been identified [Ron, D. and Mochly-Rosen, D., *Proc. Natl. Acad. Sci. USA* 92:492-496, (1995); Dorn, G. W., et al., *Proc. Natl. Acad. Sci. USA* 96:12798-12803, (1999)]. Peptides that mimic the PKC-binding site on RACKs [Mochly-Rosen, D., et al., *J. Biol. Chem.* 226:1466-1468 (1991); Mochly-Rosen, D., et al., *Science* 268:247-251 (1995)] are isozyme-specific translocation activators of PKC that selectively inhibit the function of the enzyme in vivo (Mochly-Rosen, D., *Proc. Natl. Acad. Sci. USA* 92:492-496, (1995); Dorn, G. W., et al., *Proc. Natl. Acad. Sci. USA* 96:12798-12803, (1999)). These 6-8 amino acid peptides derived from PKC are homologous to a sequence within their corresponding RACK and hence they were termed pseudo-$\beta$RACK ($\Psi\beta$RACK) and pseudo-$\epsilon$R-

ACK (ΨεRACK), respectively. Introduction of ΨβRACK or ΨεRACK into cells causes a selective translocation of the corresponding isozymes and increases their catalytic activity as measured by substrate phosphorylation in vitro and in vivo (Ron, D. and Mochly-Rosen, D., *Proc. Natl. Acad. Sci. USA* 92:492-496, (1995); Dorn, G. W., et al., *Proc. Natl. Acad. Sci. USA* 96:12798-12803, (1999)). The position in the C2 or C2-like domain of the ΨRACK sequence in isozymes whose RACK has not been identified yet (e.g., δ and θPKC) was also found to correspond to translocation agonist peptides [Chen et al., *Proc. Natl. Acad. Sci. USA* 98:1114-1119, (2001)]. For example, introduction of ΨδRACK into cells causes a selective translocation of the δPKC and increases its catalytic activity [Chen et al., *Proc. Natl. Acad. Sci. USA* 98:1114-1119, (2001)]. These peptides have also been used to identify the role of βPKC, δPKC and εPKC in cells and in vivo [Ron, D. and Mochly-Rosen, D., *Proc. Natl. Acad. Sci. USA* 92:492-496, (1995); Chen et al., *Proc. Natl. Acad. Sci. USA* 98:1114-1119, (2001); Dorn, G. W., et al., *Proc. Natl. Acad. Sci. USA* 96:12798-12803, (1999)).

From a therapeutic perspective, individual isozymes of PKC have been implicated in the mechanisms of various disease states, including the following: cancer (alpha and delta PKC); cardiac hypertrophy and heart failure (beta I and beta II PKC) nociception (gamma and epsilon PKC); ischemia including myocardial infarction (epsilon and delta PKC); immune response, particularly T-cell mediated (theta PKC); and fibroblast growth and memory (delta and zeta PKC). Various PKC isozyme- and variable region-specific peptides have been previously described (see, for example, U.S. Pat. No. 5,783,405). The role of εPKC in pain perception has recently been reported (WO 00/01415; U.S. Pat. No. 6,376,467) including therapeutic use of the εV1-2 peptide, a selective inhibitor of εPKC first described in the U.S. Pat. No. 5,783,405.

It is clear that PKC isozymes are involved in a variety of disease states, and there continues to be a need for methods of modulating the action of specific PKC isozymes to develop therapeutic agents to treat human disease.

SUMMARY OF THE INVENTION

It has been discovered that substituting at least one amino acid in a protein kinase C (PKC) agonist peptide with another amino acid to alter the charge distribution in the peptide, such as by changing the electrical charge at the substituted position, and/or such that the peptide more closely resembles a sequence within the protein kinase C binding site on the respective receptor for activated C kinase (RACK) protein will produce a PKC antagonist that may be used to inhibit the activity of the PKC enzyme. Accordingly, methods of converting a protein kinase C agonist peptide or peptidomimetic into a protein kinase C antagonist peptide or peptidomimetic are provided. In one form, a method includes substituting at least one amino acid in the agonist peptide or peptidomimetic with an amino acid that converts the PKC agonist peptide or peptidomimetic into a PKC antagonist peptide or peptidomimetic. In certain forms of the invention, the peptide antagonist is a selective inhibitor of the isozyme from which it was derived.

In yet another aspect of the invention, methods of inhibiting the activity of a PKC enzyme are also provided. In one form, a method includes contacting the enzyme with a PKC inhibitor peptide or peptidomimetic, wherein the peptide is derived from a PKC agonist peptide or peptidomimetic and wherein at least one amino acid in the agonist peptide or peptidomimetic is substituted with another amino acid sufficient to convert the agonist peptide or peptidomimetic into an antagonist peptide or peptidomimetic. In certain forms of the invention, the substitution results in a change of charge at the residue position substituted.

Treatment methods are also provided. In one form, a method includes administering a therapeutically effective amount of an εPKC antagonist peptide or peptidomimetic to a patient in need thereof. The methods may be used to treat a wide variety of diseases or conditions by modulating the activity of an εPKC enzyme.

Peptides or peptidomimetics having PKC antagonistic activity are also provided. In one form of the invention, the peptide or peptidomimetic is derived from a PKC agonist peptide or peptidomimetic wherein at least one amino acid in the agonist peptide or peptidomimetic is substituted with another amino acid sufficient to convert the agonist peptide or peptidomimetic into an antagonist peptide or peptidomimetic. In yet other forms of the invention, the peptide has the sequence as indicated herein.

It is an object of the invention to provide methods of converting a PKC agonist peptide or peptidomimetic into a protein kinase C antagonist peptide or peptidomimetic.

It is yet another object of the invention to provide methods of inhibiting the activity of a PKC enzyme.

It is yet another object of the invention to provide treatment methods using the PKC antagonists described herein.

It is a further object of the invention to provide peptides or peptidomimetics having εPKC antagonistic activity.

These and other objects and features of the invention will be more fully appreciated when the following description of the invention is read in conjunction with the accompanying drawings.

BRIEF DESCRIPTION OF THE DRAWINGS

FIGS. 2A-2C are graphs of the contraction rate of neonatal rat cardiac myocytes, expressed as the percent decrease in contraction rate relative to the basal contraction rate, as a function of time as more fully described in Example 1; where FIGS. 2A-2B show the data for cells not treated with the ePKC antagonist peptide derived from the ΨεRACK peptide (N-ΨεRACK peptide) (squares) and for cells treated with N-ΨεRACK (SEQ ID NO:2, diamonds), where both cell populations were treated with 1 nM (FIG. 2A) or 5 nM (FIG. 2B) PMA 15-20 minutes after administration of the NΨεRACK peptide; and FIG. 2C shows the data for cells treated with N-ΨεRACK peptide (diamonds) and then with ΨεRACK (SEQ ID NO:1) and with 1 nm PMA, and for cells treated with ΨεRACK (triangles) and then with 1 nM PMA.

from the cell soluble (S) to cell particulate (P) fractions of cardiac myocytes treated with a control, carrier peptide (Lane nos. 1), treated with 1 nM PMA (Lane nos. 2), treated with PMA and ΨεRACK (SEQ ID NO:1, Lane nos. 3) or treated with N-ΨεRACK, ΨεRACK, and PMA (Lane nos. 4) as more fully described in Example 2.

Figure 4:
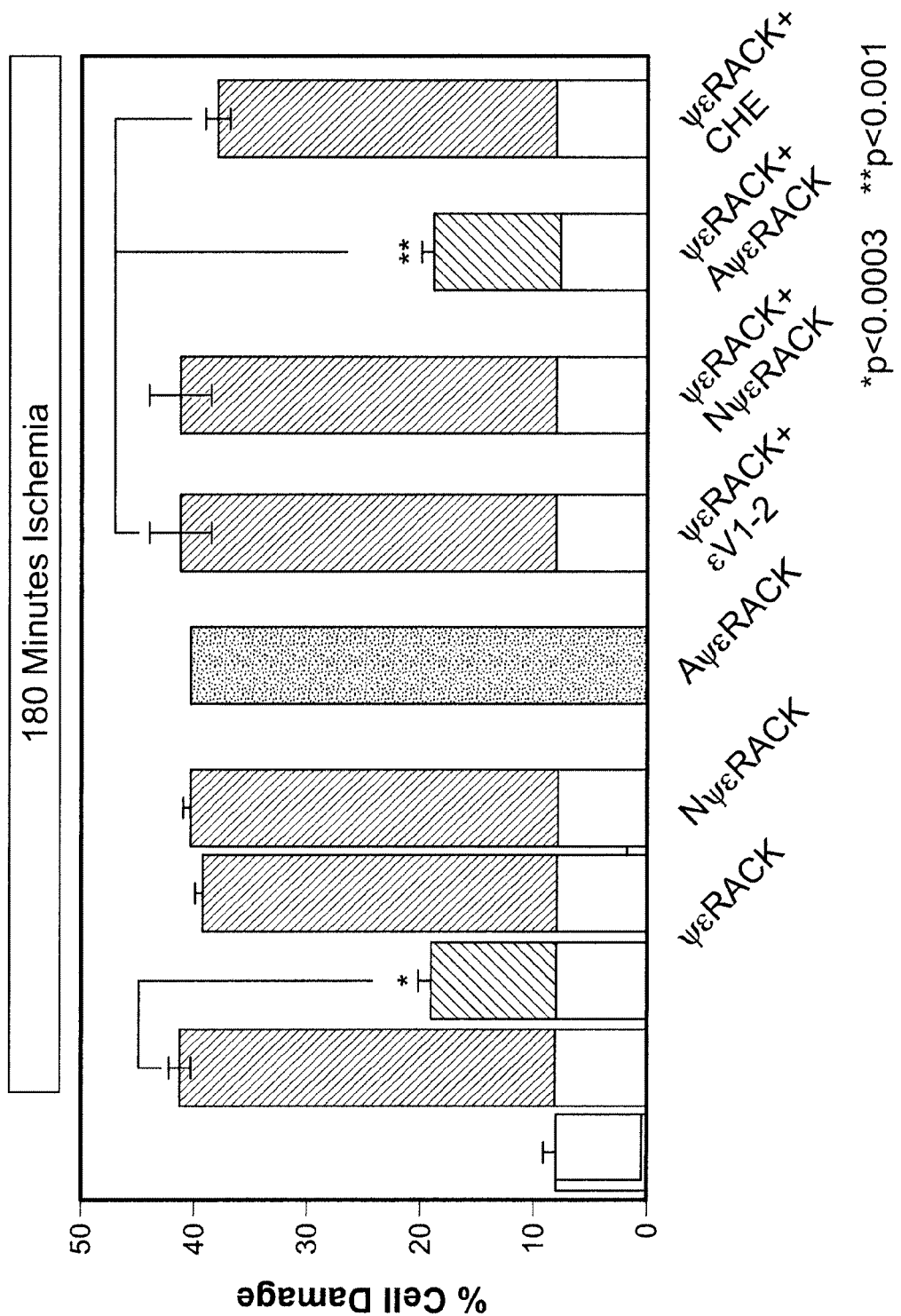

FIG. 4 is a bar graph showing the percentage of cell damage to rat cardiac myocytes resulting from an ischemic episode, where myocytes not subjected to ischemia are represented by the clear area in each bar, and the percent of ischemic damage represented by the filled area; cells were pretreated prior to the ischemic episode with ΨεRACK, N-ΨεRACK, A-ΨεRACK, εV1-2, and various combinations of these peptides as indicated as more fully described in Example 3.

Figure 5A:
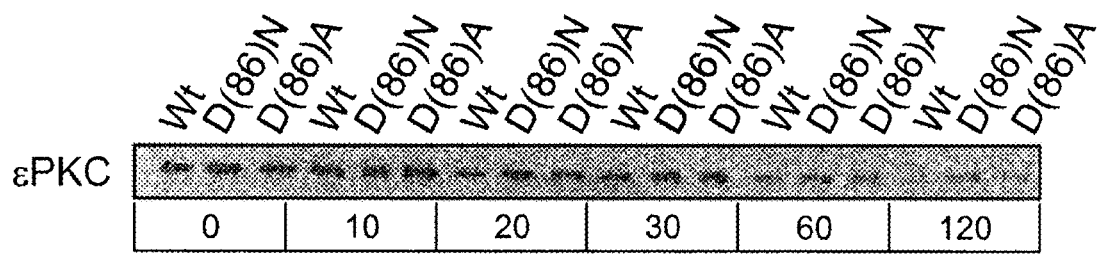

FIG. 5A depicts a Western blot analysis showing the rate of degradation of ΨεRACK mutants by the protease, Arg C, using anti-εPKCV5 antibodies as more fully described in Example 4. Wt, wild type; D(86)A, εpKC mutant wherein D at position 86 of ΨεRACK on εpKC is substituted with an A; D(86)N, εpKC mutant wherein D at position 86 of ΨεRACK in εpKC is substituted with an N.

Figure 5B:
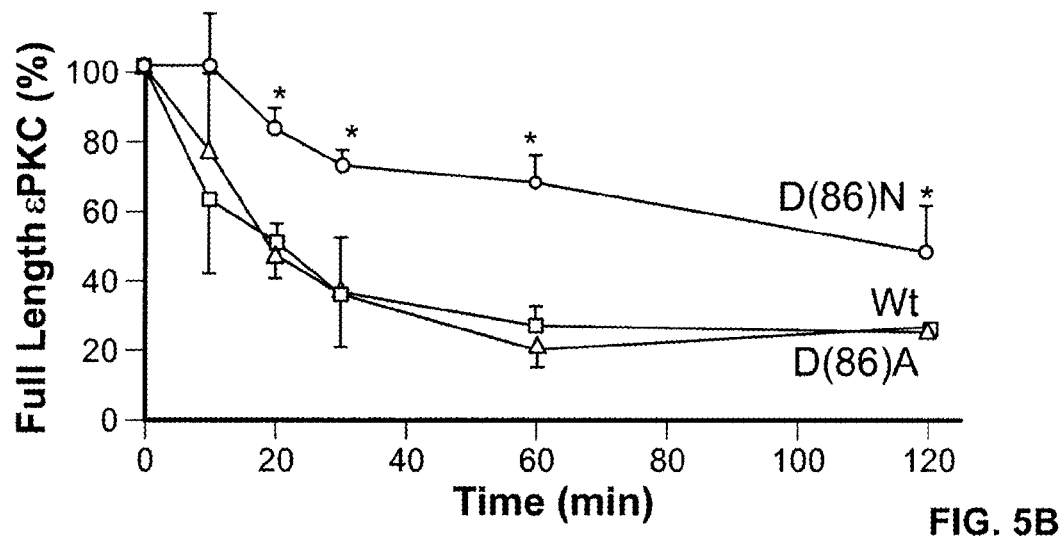

FIG. 5B depicts a graph showing the rate of degradation of the ΨεRACK εPKC mutants by Arg C as a function of time, wherein the data represents the average of five independent experiments as more fully described in Example 4. Data were normalized to the initial amount of enzyme, and are expressed as percent of full length εPKC. Wt (closed squares); D(86)A (open triangles), D(86)N (open circles); *p<0.05 using T test.

Figure 5C:
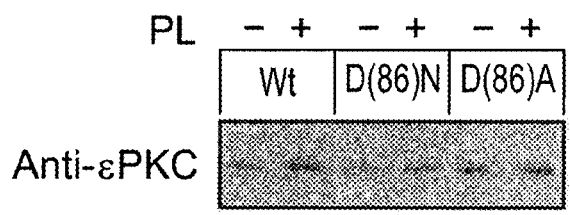

FIG. 5C depicts a Western blot analysis showing binding of ΨεRACK εPKC mutants to GST-εRACK in the presence and absence of PL as determined using anti-εPKC V5 antibodies as more fully described in Example 5. PL, phospholipid activators (phosphatidylserine and Sn-1,2 dioleoylglycerol.

Figure 5D:
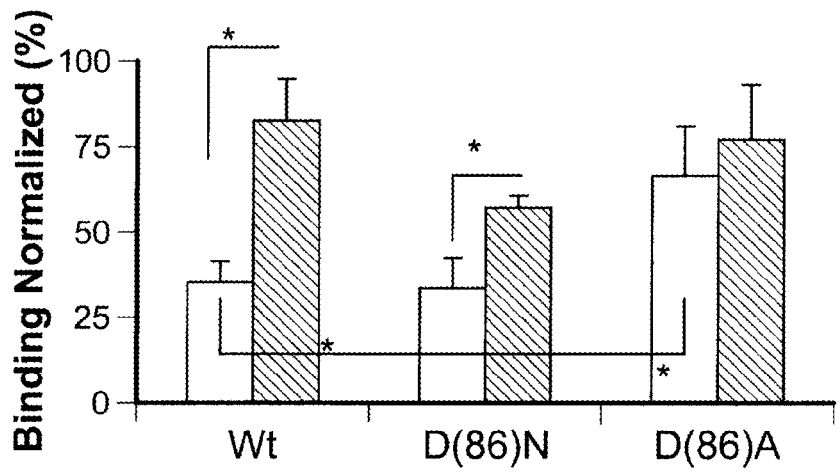

FIG. 5D depicts a graph showing normalized binding in PKC wild type and mutants (average of four independent experiments) for binding of ΨεRACK εPKC mutants to GST-εRACK, in the absence (plain bars) or presence of PL (filled bars) (*p<0.05 using T test) as more fully described in Example 5. PL, phospholipid activators (phosphatidylserine and Sn-1,2 dioleoylglycerol.

Figure 6A:
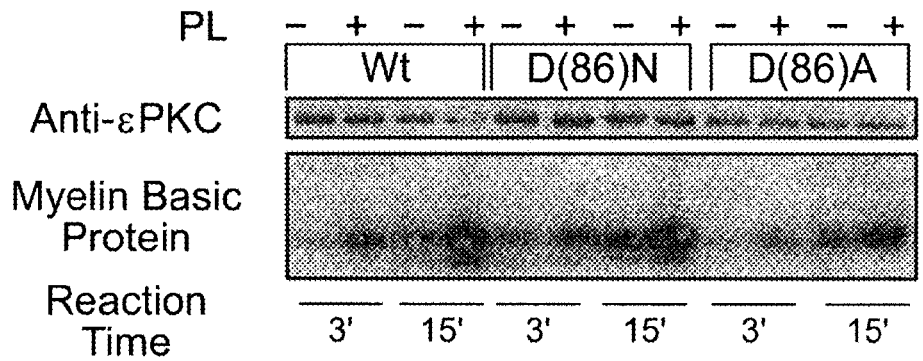

FIG. 6A shows a Western blot analysis of Immunoprecipitated GFP-εPKC mutants detected with anti-εPKC V5 antibodies (upper panel) and their catalytic activity measured by autoradiography of [$\gamma^{32}$P] labeled myelin basic protein (lower panel, a representative experiment) as more fully described in Example 6.

Figure 6B:
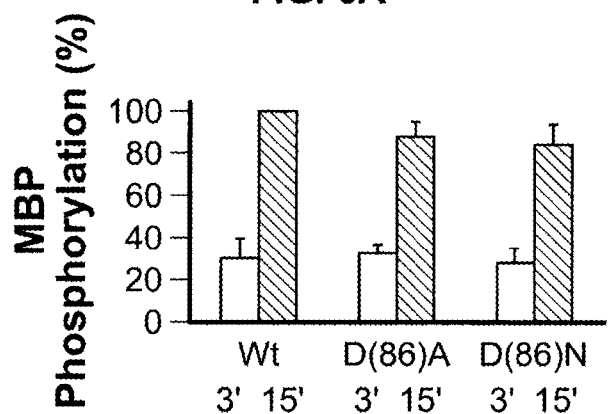

FIG. 6B shows a graph of myelin basic protein (MBP) phosphorylation in εPKC wild type or mutants as more fully described in example 6 (average of three independent kinase reactions showing equal activity of the εPKC mutants upon activation as seen by myelin basic protein phosphorylation in the presence of PL (reactions were carried out for 3 and 15 minutes).

Figure 6C:
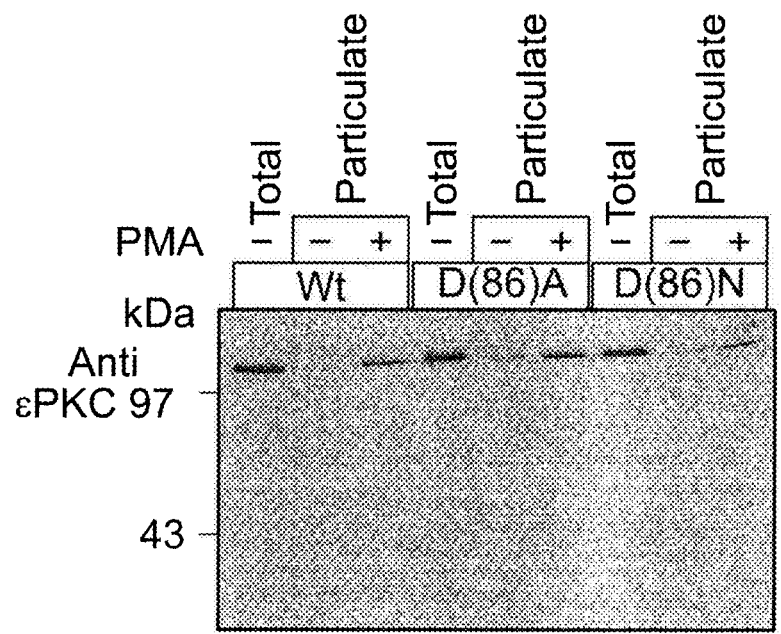

FIG. 6C depicts a Western blot analysis showing translocation of CHO cells transfected with GFP-εPKC ΨεRACK mutants and treated with 100 nM PMA for 10 minutes as more fully described in Example 6. GFP-εPKC was detedted with anti-εPKC V5 antibodies.

Figure 6D:
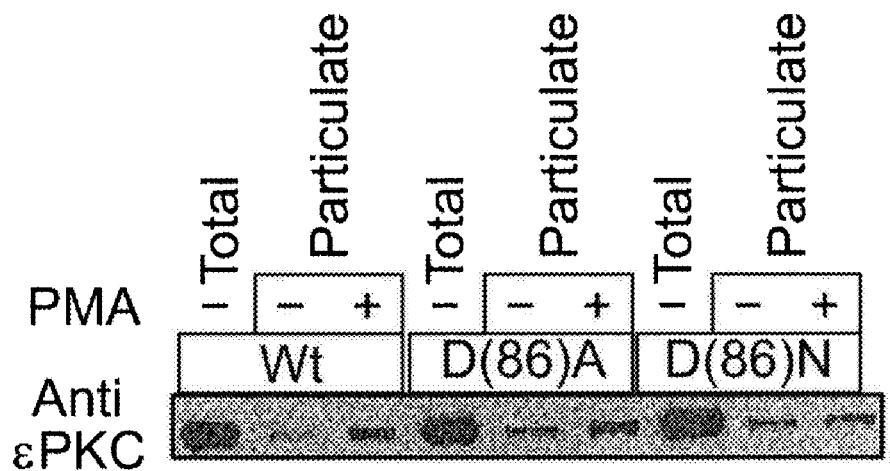

FIG. 6D shows a Western blot analysis depicting translocation of GFP-εPKC mutants in MCF-7 cells upon stimulation with 10 nM PMA for 10 minutes as more fully described in Example 6.

Figure 6E:
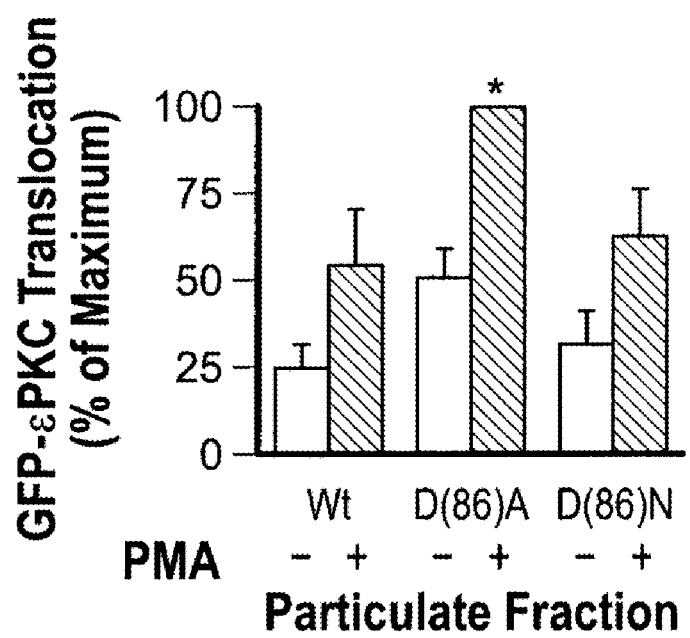

FIG. 6E shows a graph of GFP-εPKC translocation in Wt, or D(86)N mutants or D(86)A mutants after PMA stimulation as more fully described in Example 6. An average of 4 independent experiments of translocation of GFP-εPKC ΨεRACK in MCF-7 control (plain bars) and cells stimulated with 10 nM PMA for 10 minutes (filled bars) (*p<0.05 using T test) is shown in the figure.

Figure 7A:
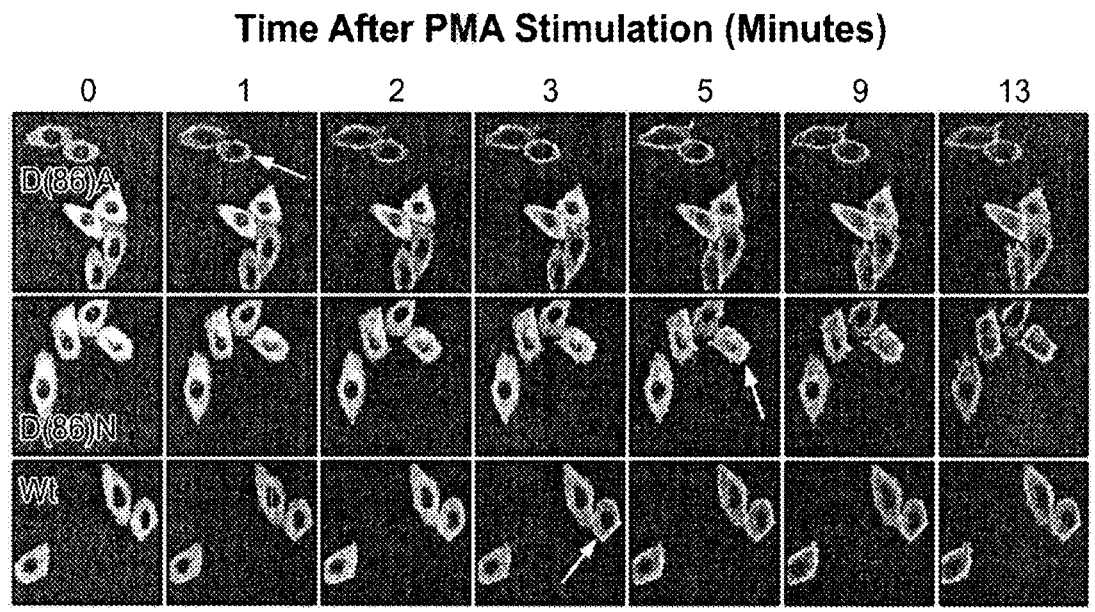

FIG. 7A depicts confocal images of ΨεRACK εPKC mutants at different time points upon stimulation with 100 nM PMA as more fully described in Example 6. An arrow within a panel indicates the time at which translocation to the cell periphery began to be apparent for each εPKC mutant.

Figure 7B:
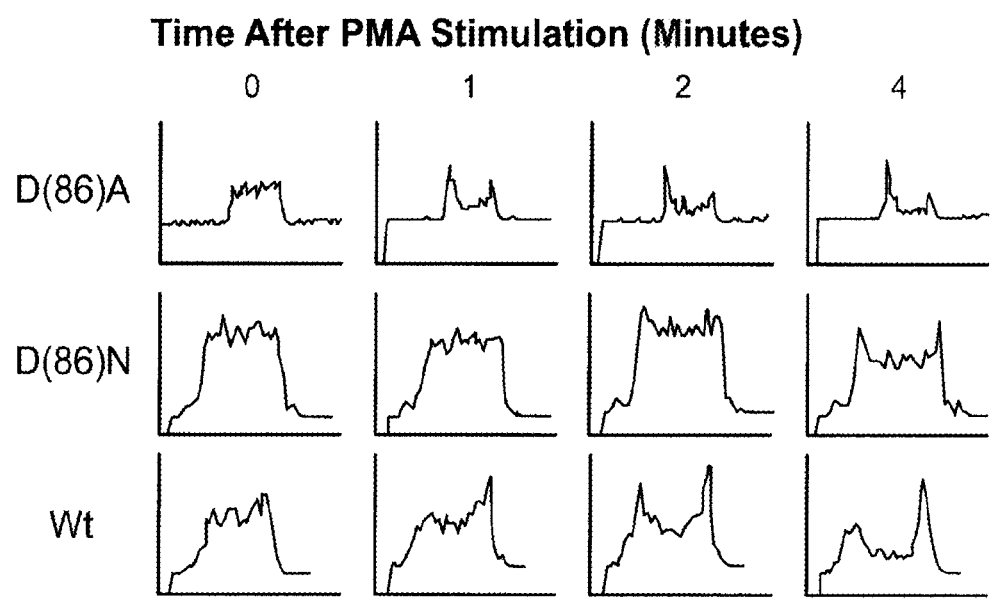

FIG. 7B depicts a typical line-intensity profile showing the distribution of PKC between the cell periphery and cytosol for representative transfected cells at different time points (indicated by a line in A, left panels) as more fully described in Example 7.

Figure 7C:
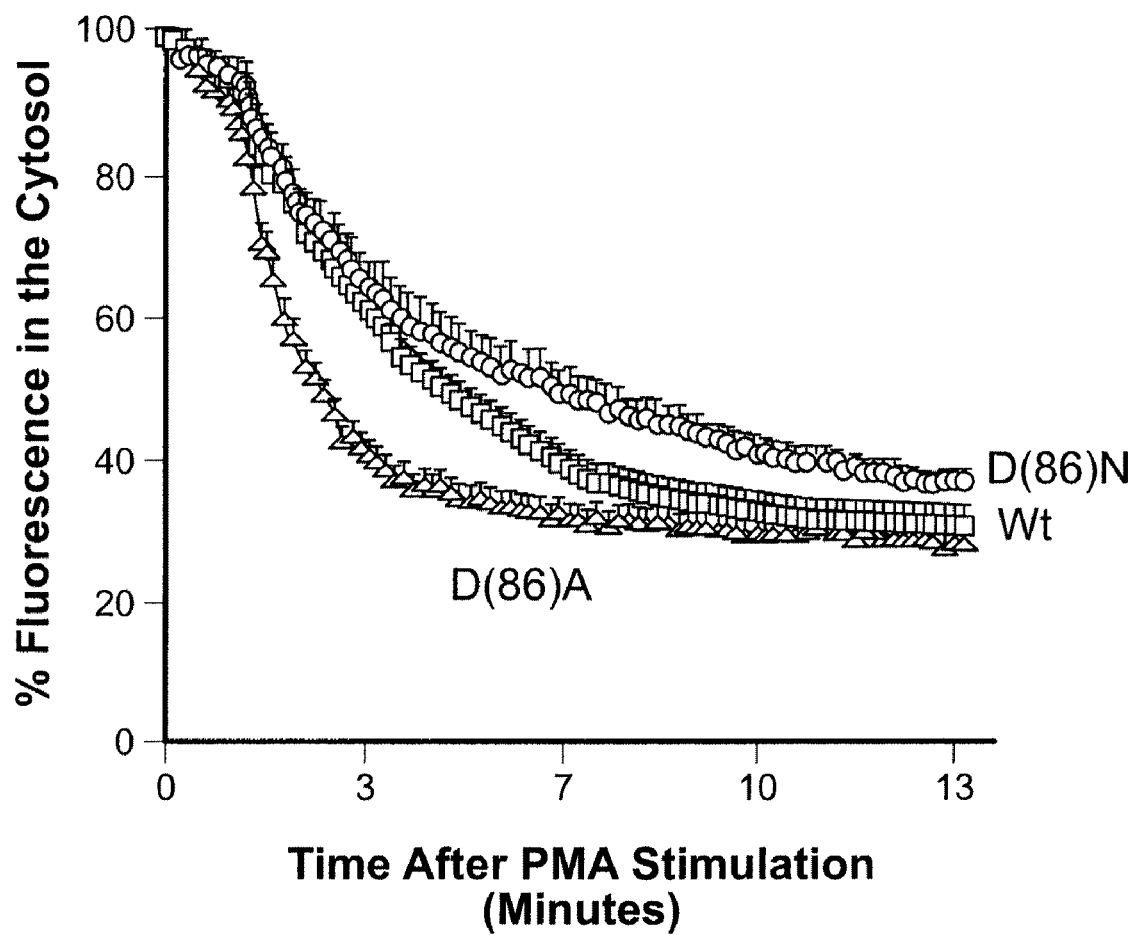

FIG. 7C depicts a graph of percent fluorescence in the cytosol of Wt cells or D(86)A or D(86)N ΨεRACK εPKC mutants as a function of time after stimulation with 100 nM PMA as more fully described in Example 6: Wt (closed squares), D(86)A (open triangle); D(86)N (open circle). Average translocation rates were expressed by normalizing the initial fluorescence intensity to 100% (average of at least three independent experiments, with at least three cells analyzed for each experiment). The time courses for the mutants and Wt enzymes were statistically different from each other by 2 way ANOVA with p<0.001.

Figure 8A:
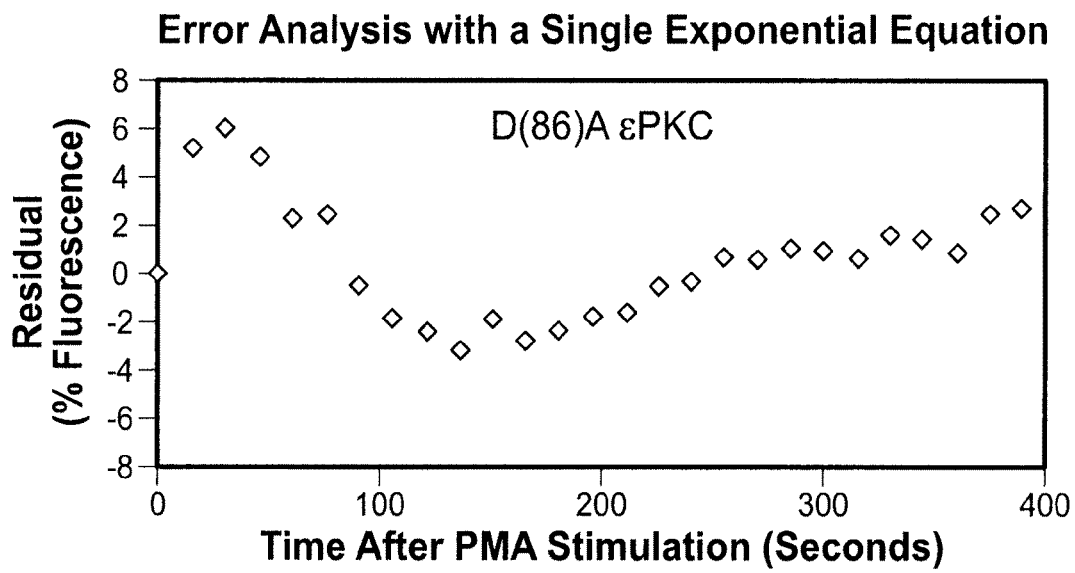
Figure 8B:
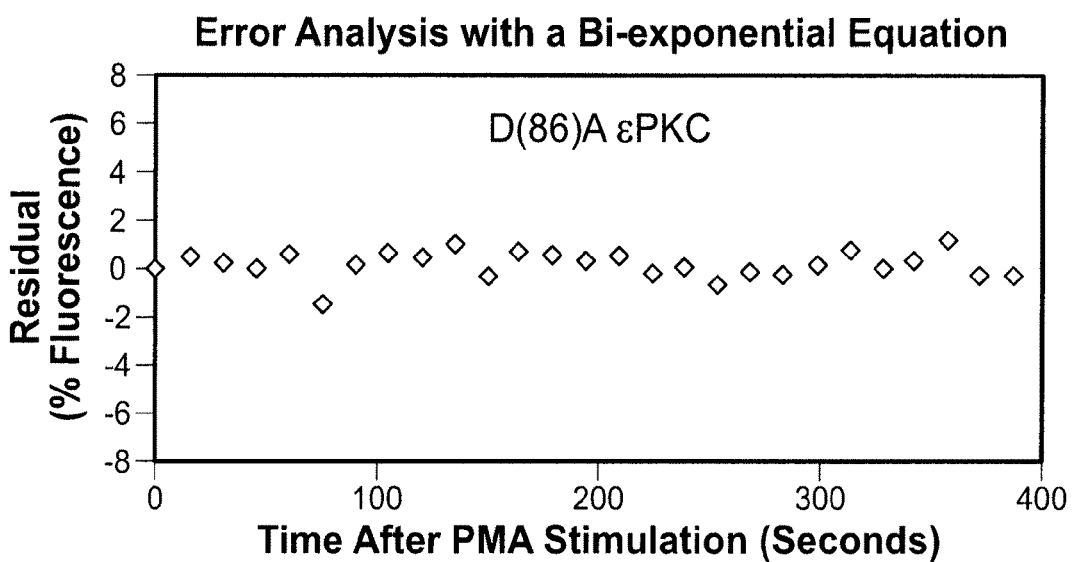
Figure 8C:
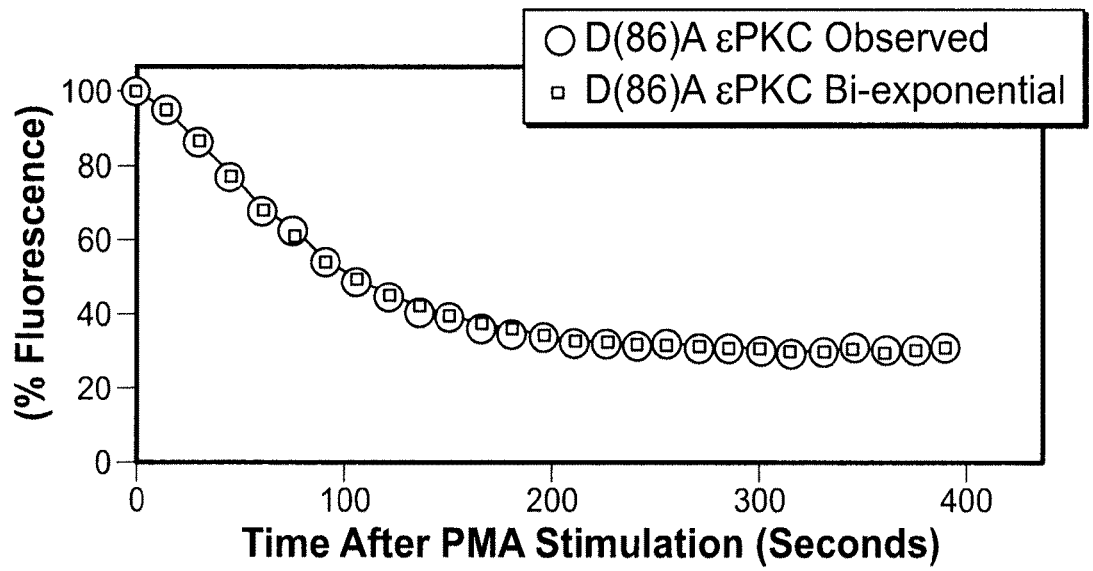
Figure 8D:
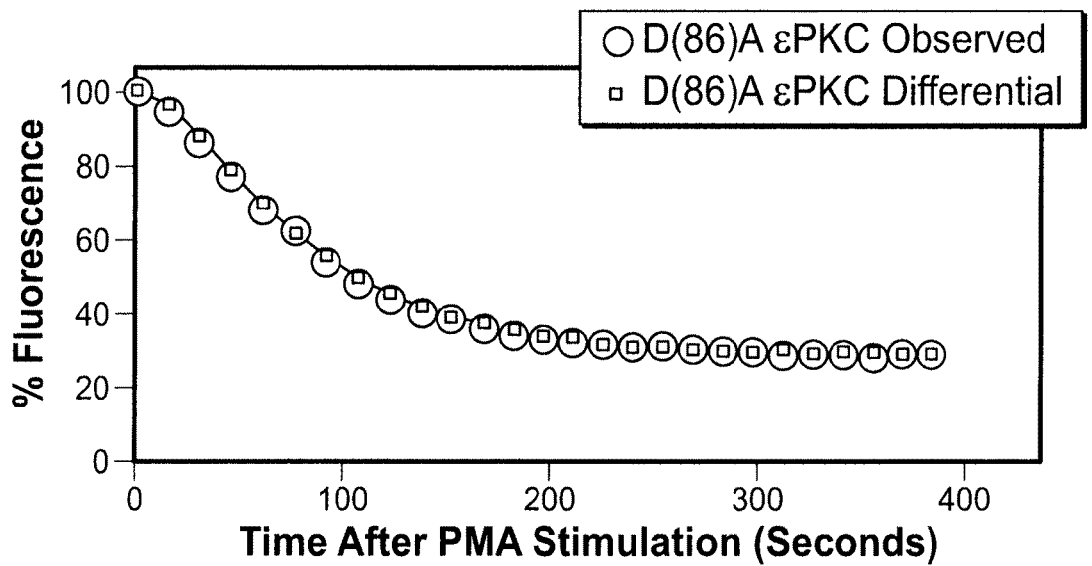

FIGS. 8A-8D depicts mathematical modeling analysis of D(86)A and analyzed as a graphical representation of percent fluorescence as a function of time after PMA stimulation as more fully described in Example 7. Similar results were obtained with D(86)N and Wt εPKC. FIG. 8A depicts non-linear regression analysis using the single exponential equation; FIG. 8B depicts non-linear regression analysis using the bi-exponential equation; FIG. 8C is a graphical representation of fit between curves of the raw data for D(86)A. The curves were obtained by nonlinear regression with a bi-exponential equation; FIG. 8D is a graphical representation of the fit between curves of the raw data for D(86)A. The curves were obtained by a differential equation using the values for k1, k-1, k2 and k-2 provided in Table 1. The residual error for all curves fitted data was similar to the one obtained with a non-linear regression using a bi-exponential equation.

Figure 9A:
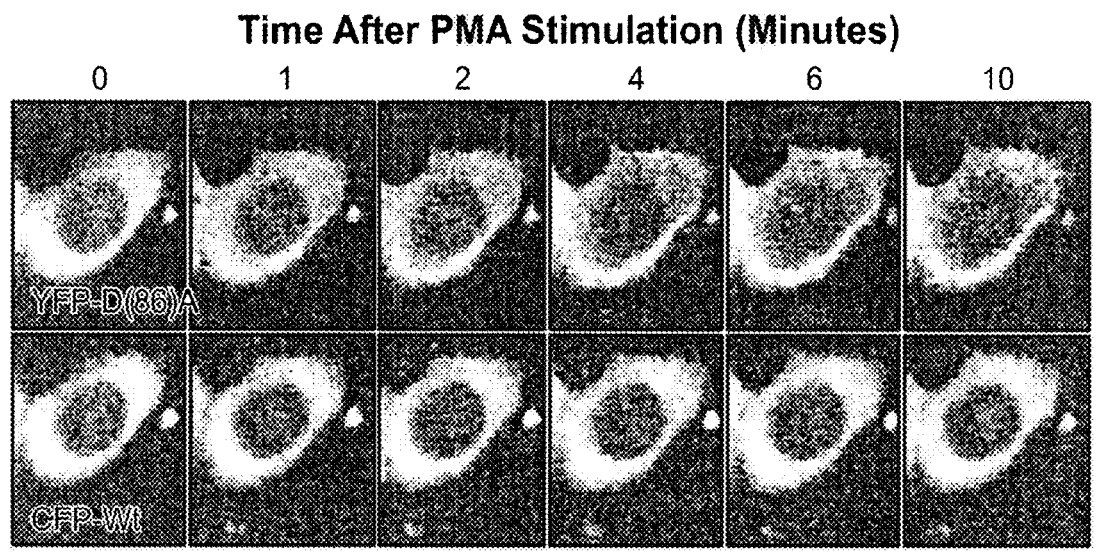

FIG. 9A depicts confocal images of CHO cells, transfected with both YFP-εPKC D(86)A and CFP-εPKC Wt, at different times after stimulation with 100 nM PMA as more fully described in Example 8.

Figure 9B:
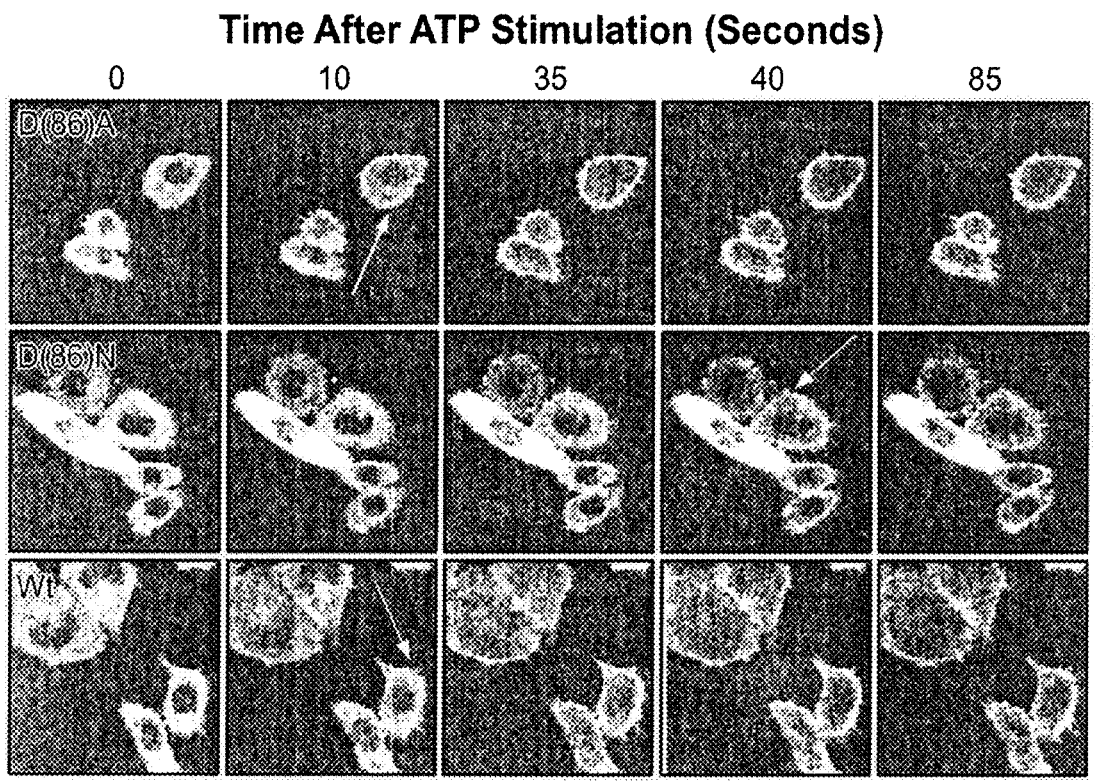

FIG. 9B depicts confocal images of CHO cells, transfected with D(86)A and D(86(N) mutants, as a function of time after being stimulated with 1 mM ATP as more fully described in Example 9. In comparison to wild type, the D(86)A mutant had a similar translocation rate and the RACK D(86)N mutant had a slower translocation rate upon stimulation with 1 mM ATP. The arrows indicate the time at which translocation to the cell periphery began to be apparent for each εPKC enzyme.

Figure 9C:
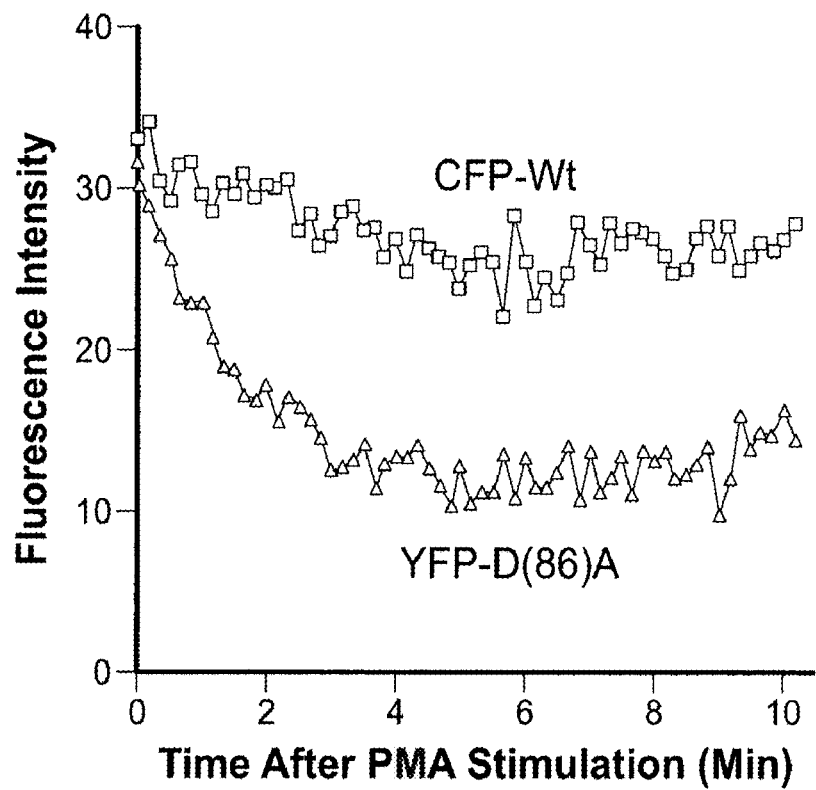

FIG. 9C depicts fluorescence intensity as a function of time after PMA stimulation in cells transfected with D(86)A and D(86(N) as more fully described in Example 9. Translocation rates were analyzed by measuring the loss of fluorescence in the cytoplasm relative to time after addition of 1 mM ATP: Wt (closed square), D(86)A (open triangle), D(86)N (open circle). Data are averages of at least three independent experiments with at least three cells in each experiment. The time course for the D(86)N mutant was statistically different from either D(86)A or Wt εPKCs using a 2 way ANOVA test with p<0.001.

Figure 9D:
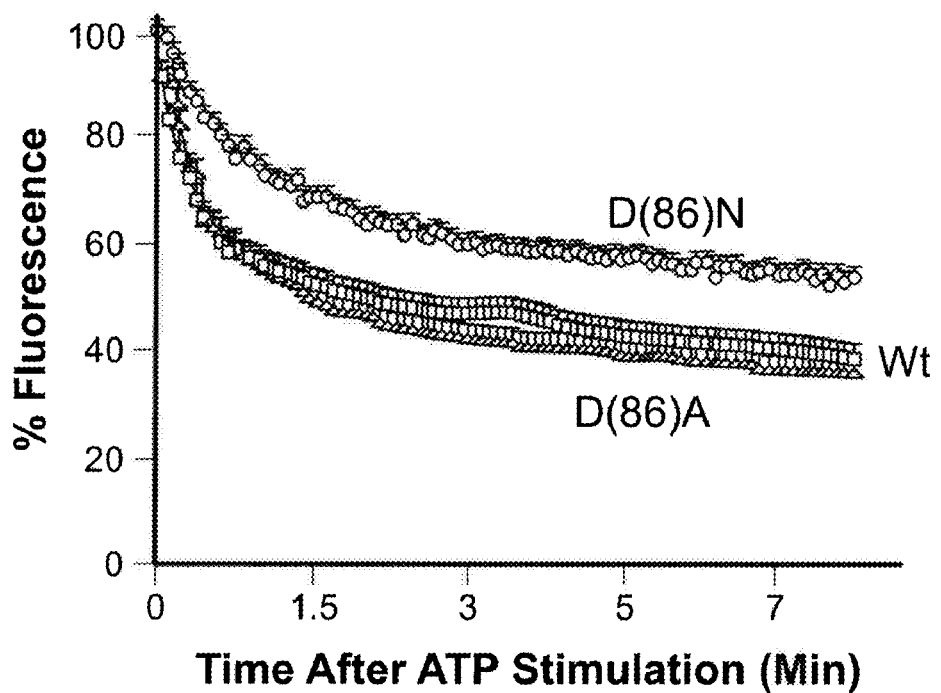

FIG. 9D depicts fluorescence intensity as a function of time after ATP stimulation of CHO cells transfected CFP-εPKC Wt.(closed square) and YFP-εPKC D(86)A (open triangle) as more fully described in Example 8. Levels of the YFP-εPKC D(86)A mutant in the cytoplasm decrease faster than levels of CFP-εPKC Wt.

Figure 10:
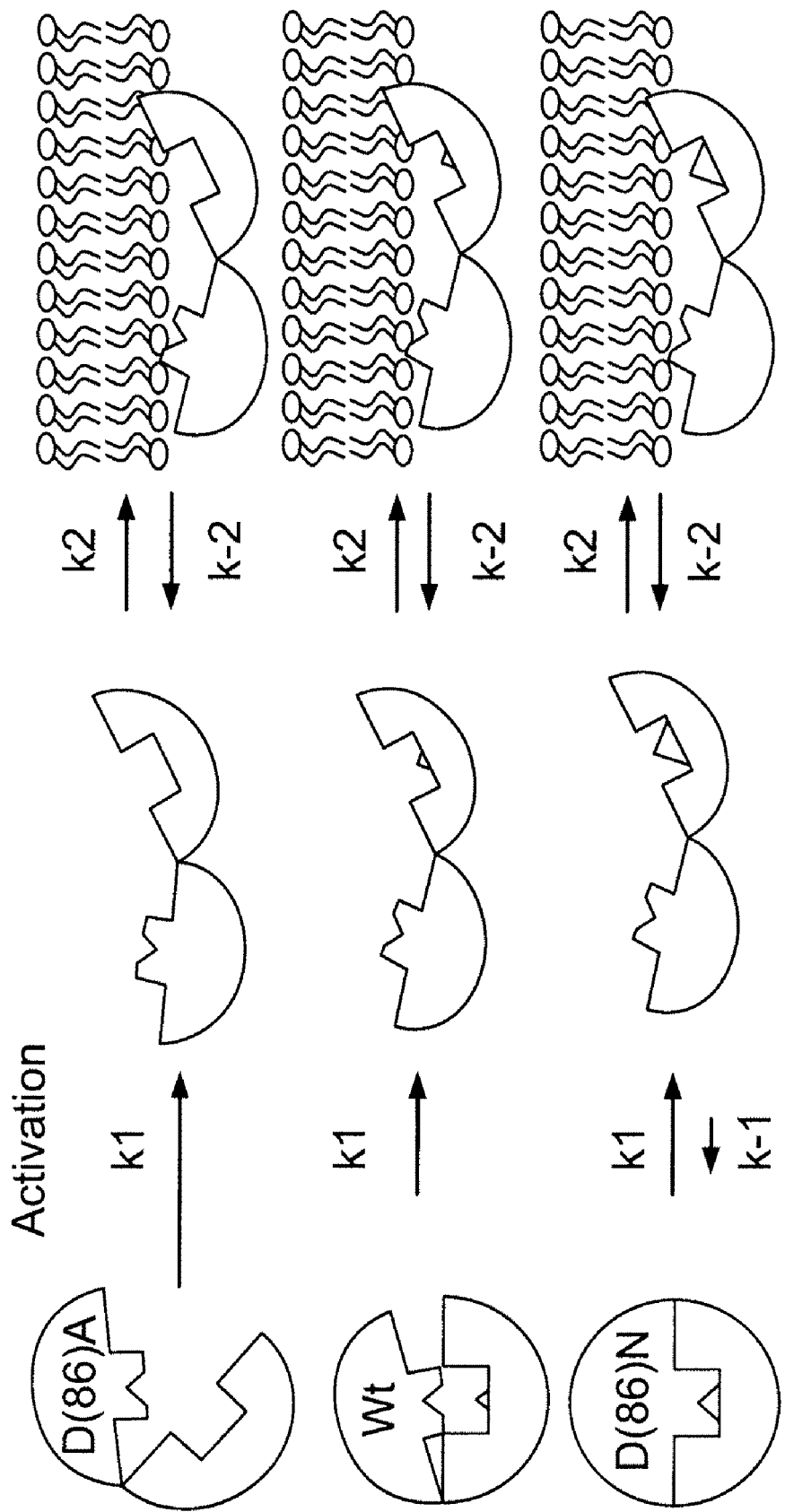

FIG. 10 depicts a pictorial showing the first steps in εPKC translocation to the membrane upon activation; a two-step process, as more fully described in the Discussion section of the Examples. An additional step in the process of translocation includes binding to the RACK (not shown in the scheme). For simplicity, only the intramolecular interaction between the ΨεRACK and the εRACK-binding site are shown.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention provides methods of converting a PKC agonist peptide or peptidomimetic into a PKC antagonist peptide or peptidomimetic. It has been discovered that substituting at least one amino acid in a PKC agonist peptide or peptidomimetic with another amino acid such that the charge distribution of the peptide or peptidomimetic is changed and/or such that the peptide or peptidomimetic more closely resembles a sequence within the PKC binding site on the respective RACK protein will produce an antagonist that may be used to inhibit the activity of the PKC enzyme. In one form, a method includes substituting at least one amino acid in the agonist peptide or peptidomimetic with an amino acid that converts the PKC agonist peptide or peptidomimetic into a PKC antagonist peptide or peptidomimetic. In yet other forms of the invention, the substitution may be made by synthesizing a peptide or peptidomimetic having the different amino acid or by modifying an amino acid in a pre-existing peptide or peptidomimetic such that the agonist peptide or peptidomimetic is converted into an antagonist peptide or peptidomimetic. The peptidomimetic herein includes a small molecule that selectively binds to the intermolecular binding site on the respective PKC enzyme.

Methods of inhibiting the activity of a protein kinase C (PKC) enzyme are also provided. In one form, a method includes contacting the PKC enzyme with a PKC inhibitor peptide or peptidomimetic derived from a PKC agonist peptide or peptidomimetic wherein at least one amino acid in the agonist peptide or peptidomimetic is substituted with another amino acid sufficient to convert the agonist peptide or peptidomimetic into an antagonist peptide or peptidomimetic.

Treatment methods are also provided. In one form, a method includes administering a therapeutically effective amount of an εPKC antagonist peptide or peptidomimetic to a patient in need thereof. The methods may be used to treat a wide variety of diseases or conditions by modulating the activity of an εPKC enzyme.

Peptides or peptidomimetics having PKC antagonistic activity are also provided. In certain forms of the invention the peptide or peptidomimetic is derived from a PKC agonist peptide or peptidomimetic wherein at least one amino acid in the agonist peptide or peptidomimetic is substituted with another amino acid sufficient to convert the agonist peptide or peptidomimetic into an antagonist peptide or peptidomimetic.

In one aspect of the invention, methods of converting a PKC enzyme agonist peptide or peptidomimetic into a PKC enzyme antagonist peptide or peptidomimetic are provided. In one form, a method includes substituting at least one amino acid in a PKC agonist peptide or peptidomimetic with another amino acid sufficient to convert the PKC agonist into a PKC antagonist. "Peptide" and "polypeptide" as used herein refer to a compound made up of a chain of amino acid residues linked by peptide bonds. Unless otherwise indicated, the sequence for peptides is given in the order from the amino terminus to the carboxyl terminus.

The method is applicable to a wide variety of PKC enzymes. As described above, PKC enzymes are classified into three families based on the homology of their regulatory domains: conventional PKC (cPKC; including $\alpha$, $\beta_I$, $\beta_{II}$, and $\gamma$), novel PKC (nPKC; including $\epsilon$, $\delta$, $\eta$, and $\theta$) and atypical PKC (aPKC; including $\xi$, $\iota$, and $\lambda$). As previously mentioned herein, in order for the PKC enzymes to exert their biological effects, they must be activated and bind to their respective RACK proteins. As an example, an εPKC binding site exists on εRACK (the amino acid sequence of which is set forth in SEQ ID NO:1 as NNVALGYD). PKC binding sites also exist on other RACKS for binding interactions with their respective PKC enzymes. For example, the βPKC binding site on RACK1 is set forth in SEQ ID NO:2 as SIKIWD. This sequence is identical between $\beta_I$ and $\beta_{II}$ since they differ only in the last 50 amino acids and is identical in $\alpha$ and $\gamma$PKC. In one form of the invention when designing a particular antagonist from a specified agonist, these binding site sequences can be referred to in order to ensure the at least one amino acid is substituted with an amino acid that makes the peptide or peptidomimetic more closely resemble the PKC binding site on the respective PKC enzymes or to otherwise increase the binding affinity of the peptide or peptidomimetic to the binding site. In yet other forms of the invention, substituting at least one charged amino acid in the peptide agonists or peptidomimetics described herein with an uncharged amino acid is expected to convert the PKC agonist into a PKC antagonist.

A wide variety of PKC peptide or peptidomimetic agonists may be modified or otherwise converted into a PKC antagonist peptide or peptidomimetic and consequently find use in the invention. The PKC agonists may include a sequence of at least about 4 to about 30 amino acids or at least about 5 to about 15 amino acids. It is realized that the PKC agonists may be composed of sequences longer than about 30 amino acids. By "PKC agonist", it is meant herein a compound that activates a PKC to form an activated PKC, facilitates or allows PKC to perform its biological functions, or mimics the activity of a PKC to allow the mimic to carry out one or more of the biological functions of PKC. The agonists may, for example, allow activated PKC to be translocated to specific areas of the cell so that it may exert its biological effect. As known in the art, the PKC family of enzymes are serine/threonine kinases and are involved in a myriad of cellular process, including cell growth, regulation of gene expression, and ion channel activity. By "PKC antagonist" or "PKC inhibitor", it is meant herein a compound that inhibits a PKC enzyme to form a deactivated PKC enzyme, prevents or facilitates prevention of PKC from performing its biological functions, or mimics the activity of a PKC antagonist to allow the mimic to inhibit the biological functions of PKC. The antagonists may, for example, prevent activated PKC from being translocated to specific areas of the cell so that the PKC may be prevented from exerting its biological effect. It is noted that the terms "antagonist" and "inhibitor" are used interchangeably herein.

Such agonists include cPKC agonists, such as αPKC agonists, $\beta_I$PKC agonists, $\beta_{II}$PKC agonists, and γPKC agonists;

nPKC agonists, including εPKC agonists, δPKC agonists, ηPKC agonists, and θPKC agonists; and aPKC agonists, including ξPKC agonists, ιPKC agonists and λPKC agonists. The respective PKC agonists may be derived from the ΨRACK sequences present in the respective PKC enzymes (e.g., ΨαRACK, Ψβ,RACK, ΨεRACK, ΨλRACK, etc.). A peptide or peptide fragment is "derived from" a parent peptide or polypeptide if it has an amino acid sequence that is identical or otherwise has a specified percent identity to the amino acid sequence of the parent peptide or polypeptide, including at least about 30%, at least about 40%, at least about 50%, at least about 60%, at least about 70%, at least about 80%, at least about 90% and at least about 95% identity. Such a definition includes peptides or peptidomimetics that have at least one amino acid substitution therein when compared to the parent peptide, polypeptide or peptidomimetic. Although not being limited by theory, these ΨRACK sequences have been found herein to be involved in at least inhibitory intramolecular interactions with the respective RACK binding site in a PKC enzyme as more fully discussed in the Examples herein.

Percent identity may be determined, for example, by comparing sequence information using the advanced BLAST computer program, including version 2.2.9, available from the National Institutes of Health. The BLAST program is based on the alignment method of Karlin and Altschul. *Proc. Natl. Acad. Sci. USA* 87:2264-2268 (1990) and as discussed in Altschul, et al., *J. Mol. Biol.* 215:403-410 (1990); Karlin And. Altschul, *Proc. Natl. Acad. Sci. USA* 90:5873-5877 (1993); and Altschul et al., *Nucleic Acids Res.* 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the proteins being compared. Default parameters are provided to optimize searches with short query sequences in, for example, blastp with the program. The program also allows use of an SEG filter to mask-off segments of the query sequences as determined by the SEG program of Wootton and Federhen, *Computers and Chemistry* 17:149-163 (1993).

A wide variety of such ΨRACK sequences are known in the art in a variety of species including the following human sequences, such as ΨεRACK (HDAPIGYD, SEQ ID NO:3); ΨδRACK (MRAAEEPM, SEQ ID NO:4); ΨθRACK (KGKNVDLI, SEQ ID NO:5); ΨηRACK (HETPLGYD, SEQ ID NO:6); and ΨβRACK (SVEIWD, SEQ ID NO:7). RACK sequences were identified by searching for regions of homology between each PKC isozyme and its RACK. In εPKC, for example, the ΨεRACK sequence HDAPIGYD (SEQ ID NO:3; εPKC 85-92) has approximately 75% homology with a sequence in εRACK consisting of amino acids NNVALGYD (SEQ ID NO:1; εRACK 285-292). Peptides corresponding to the ΨRACK sequences, including εPKC, function as an εPKC-selective agonist.

The agonist may be a derivative of the sequences described above, including fragments or modifications thereof. Modifications include conservative amino acid substitutions in the amino acid sequences to obtain derivatives of the peptides that may advantageously be utilized as agonists in the present invention.

Conservative amino acid substitutions are substitutions which do not result in a significant change in the activity (e.g., εPKC-agonist activity or ΨεRACK-agonist activity) or tertiary structure of a selected peptide or polypeptide. Such substitutions typically involve replacing a selected amino acid residue with a different residue having similar structure, size or other physico-chemical properties. For example, substitution of Glu for Asp is considered a conservative substitution since both are similarly-sized negatively-charged amino acids. Groupings of amino acids by physico-chemical properties are known to those of skill in the art. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine.

Accordingly, suitable εPKC agonists derived from the ΨεRACK sequence of εPKC, include, for example, HDAPIGYD (SEQ ID NO:3) and modifications and/or fragments thereof, including the following sequences: SEQ ID NO:8 (HEADIGYD); SEQ ID NO:9 (HDAPIGYE); SEQ ID NO:10 (HDAPVGYE); SEQ ID NO:11 (HDAPLGYE); SEQ ID NO:12 (HDAPIGDY); SEQ ID NO:13 (HDAPIGEY); SEQ ID NO:14 (ADAPIGYD); SEQ ID NO:15 (HDGPIGYD); SEQ ID NO:16 (HDAAIGYD); SEQ ID NO:17 (AEAPVGEY); SEQ ID NO:18 (HEAPIGDN); SEQ ID NO:19 (HDGDIGYD); SEQ ID NO:20 (HDAPIG) and SEQ ID NO:21 (HDAPIPYD).

Suitable δPKC agonists derived from the ΨδRACK sequence of δPKC include, for example, SEQ ID NO:4 (MRAAEEPV) and modifications and/or fragments thereof, including the following sequences: SEQ ID NO:22 (MRVAEEPV); SEQ ID NO:23 (MRWEEPV); SEQ ID NO:24 (MRAADEPV); SEQ ID NO:25 (MRAAEEP); SEQ ID NO:26 (MRLLEEPV); SEQ ID NO:27 (MRLAEEPV); and SEQ ID NO:28 (MRAAEE).

Exemplary ηPKC agonists derived from the ΨηRACK sequence on ηPKC include, for example, HETPLGYD (SEQ ID NO:6) and modifications and/or fragments thereof, including the following sequences: SEQ ID NO:29 (HDTPLGYD); SEQ ID NO:30 (HDTPLG); SEQ ID NO:31 (HDTPIGYD); SEQ ID NO:32 (HETPAGYD); SEQ ID NO:33 (HETPAGYE); SEQ ID NO:34 (KETPAGYD); SEQ ID NO:35 (KETPVGYD) and SEQ ID NO:36 (KETPVG).

Exemplary θPKC agonists derived from the ΨθRACK sequence on θPKC include, for example, KGKNVDLI (SEQ ID NO:5) and modifications and/or fragments thereof, including the following sequences: SEQ ID NO:37 (RGKNVELA); SEQ ID NO:38 (KNVDLI); SEQ ID NO:39 (RGRNVDLI; SEQ ID NO:40 (KGRNADLI; SEQ ID NO:41 (KGKNVELI); SEQ ID NO:42 (KGKNVELA); SEQ ID NO:43 (KGKQVDLI) and SEQ ID NO:44 (RGKNLDLI).

Exemplary βPKC agonists derived from the ΨβRACK sequence on βPKC include, for example, SVEIWD (SEQ ID NO:7) and modifications and/or fragments thereof, including the following sequences: SEQ ID NO:45 (SAEIWD); SEQ ID NO:46 (SVELWD); SEQ ID NO:47 (TVEIWD); SEQ ID NO:48 (SVEIWE) and SEQ ID NO:49 (SVEIW).

It is appreciated that other suitable agonists include those have at least about 50% identity, further at least about 60% identity, at least about 70% identity, further at least about 80% identity and further at least about 90% identity to the amino acid sequences of the agonists described herein, including SEQ ID NOs:3-49 and that function as agonists for the respective PKC enzymes.

It will be also appreciated that the ΨRACK sequences described herein may also include one or more amino acid residues beyond the residues shown herein. For example, with respect to the ΨεRACK sequence at positions 85-92 (corresponding to the sequence HDAPIGYD; SEQ ID NO:3), SEQ ID NO:93 (TDVCNGRKIELAVFHDAPIGYDDF-VANCTI) shows the sequence of residues from amino acids 71-100 in εPKC. Regarding the ΨδRACK sequence at positions 74-81 (corresponding to the sequence MRAAEEPV; SEQ ID NO:4), SEQ ID NO:94 (IQIVLM-RAAEEPVSEVTV) shows the sequence of residues from amino acids 69-86 in δPKC. Regarding the ΨθRACK sequence at positions 75-82 (corresponding to the sequence KGKNVDLI; SEQ ID NO:5), SEQ ID NO:95 (MQI-IVKGKNVDLISETTV) shows the sequence of residues from amino acids 70-87 in θPKC. Regarding the ΨηRACK sequence at positions 88-95 (corresponding to the sequence HETPLGYD; SEQ ID NO:6), SEQ ID NO:96 (ELAVFHET-PLGYDHFVAN) shows the sequence of residues from amino acids 83-100 in ηPKC. Regarding the ΨβRACK sequence at positions 241-246 (corresponding to the sequence SVEIWD; SEQ ID NO:7), SEQ ID NO:97 (KDRRLSVEIWDWD-WDL) shows the sequence of residues from amino acids 236-251 in βPKC. Sequences derived from SEQ ID NOs:93-96 and having activity as an εPKC, δPKC, θPKC and ηPKC agonist, for example, can be modified according to the teachings herein to convert the biological activity to that of an antagonist by selecting replacement amino acids that effect a change of charge in the peptide at the location of the substitution, such as by decreasing or increasing the electrical charge at the location of substitution. For example, a negatively or positively-charged amino acid may be substituted for an uncharged amino acid. In certain forms of the invention, the modified sequence more closely resembles the charge distribution of the native RACK for the respective enzyme.

The amino acid present in the PKC agonist peptide that is sufficient to convert the PKC agonist into a PKC antagonist is, in one form of the invention, an amino acid that makes the agonist peptide more closely resemble a sequence within the PKC binding site on the respective RACK protein. Accordingly, the substitution will be at a particular location on the agonist peptide and with an amino acid that increases the percent identity between the PKC agonist and the reference sequence within the PKC binding site on the respective RACK protein when compared to the percent identity between the two sequences prior to the substitution. Such an amino acid that replaces the substituted amino acid may include one that would provide a non-conservative amino acid substitution in the peptide.

The reference sequence on the RACK protein that the peptide sequence is compared to is one that is derived from optimally aligning the two sequences being compared using the BLAST program previously described herein or other similar programs known in the art, and may represent, for example, a sequence of about 4 to about 30 amino acids or about 5 to about 15 amino acids. It is realized that reference sequences longer than 30 amino acids in the PKC binding site of the respective RACKs may also be utilized when comparing the peptide antagonist being constructed to the reference sequence, including in situations wherein the length of the peptide antagonist is longer than about 30 amino acids. Examples of such sequences wherein reference sequences may be selected from for various isotypes of PKC discussed herein has been previously enumerated herein. The amino acid that is substituted can be any amino acid in the peptide that, when substituted with another appropriate amino acid as described herein, will result in a peptide sequence having increased percent identity to a sequence within the PKC binding site on the RACK protein of the PKC enzyme and, consequently, will result in conversion of the PKC agonist peptide into a PKC antagonist peptide. This appropriate amino acid includes an amino acid that increases the binding affinity between the peptide or peptidomimetic and the PKC binding site on the RACK protein of the PKC enzyme.

In other forms of the invention, the amino acid that is sufficient to convert the PKC agonist into a PKC antagonist is an amino acid that allows the peptide or peptidomimetic to more closely approximate the charge distribution in a reference peptide chosen from the PKC binding site on its respective RACK protein or where one substitutes a charged amino acid with an uncharged amino acid. Such an amino acid that replaces the substituted amino acid may be one that would provide a non-conservative amino acid substitution in the peptide. As an example, if a reference peptide of 8 amino acids has an uncharged amino acid at position 2, and the agonist has a charged amino acid in the same position when optimally aligned using the BLAST program, the amino acid in the agonist may be substituted with an uncharged amino acid in order to allow the agonist peptide to more closely approximate the charge at a particular location in the reference peptide and convert the PKC agonist into an antagonist. Therefore, one may substitute a negatively charged (e.g., aspartic acid or glutamic acid) amino acid in the PKC agonist with a polar, uncharged amino acid (e.g., asparagine or glutamine), thereby decreasing the electrical charge at the location of substitution in the peptide. It will be appreciated that in some cases, a polar, uncharged residue in a given sequence may be replaced with a charged residue, such as a positively or negatively-charged amino acid residue, thereby increasing the electrical charge at the location of substitution in the peptide to effect a change in peptide function.

At least one amino acid in the agonists is substituted. In certain forms of the invention, 2, 3, or 4 amino acids or more may be substituted. The number, or percentage, of amino acids that may be substituted in the agonists may also depend on the number of amino acids in the peptide or peptidomimetic. The longer the length of the agonist, and/or the greater the difference in percent identity or charge distribution between the agonist peptide and a sequence within the PKC binding site in the respective RACK, would allow for a greater number of substitutions. A suitable number of substitutions in an agonist of about 8 amino acids includes no more than about 4. As an example, at least about 20%, at least about 30%, further at least about 40%, further at least about 50%, and at least about 60% of the amino acids in the agonist peptide or peptidomimetic may be substituted.

Exemplary peptides that may have εPKC antagonistic activity that are derived from εPKC agonist peptides according to the methods of the present invention include those set forth in SEQ ID Nos: 50-57. These antagonists are based on alternative ΨεRACK sequences identified as SEQ ID NOs: 12 (HDAPIGDY), 20 (HDAPIG), 16 (HDAAIGYD), and 21 (HDAPIPYD), which are disclosed in U.S. Pat. No. 6,165,977 and may be modified to, for example, look more similar to a sequence within the εPKC binding site on εRACK, such as, for example, NNVALGYD (SEQ ID NO:1) and/or to include a change of charge at selected amino acid residues. These alternative ΨεRACK sequences may be modified according to the method disclosed herein, wherein one or more amino acid residues can be replaced with an amino acid residue to effect a change of charge in the peptide. For example, SEQ ID NO:12 (HDAPIGDY) may be modified by substitution of N for D to arrive at SEQ ID NO:50 (HNAPIGDY) and SEQ ID NO:51 (HDAPIGNY). SEQ ID NO:20 (HDAPIG) may be modified by substitution of N for D to arrive at SEQ ID NO:52 (HNAPIG). SEQ ID NO:21 (HDAPIPYD) may be modified by substitution of N for D to arrive at SEQ ID NO:53 (HNAPIPYD) and SEQ ID NO:54 (HDAPIPYN). Additionally, SEQ ID NO:3 (HDAPIGYD) may be modified by substituting the first D for N to arrive at SEQ ID NO:55 (HNAPIGYD). SEQ ID NO:16 (HDAAIGYD) may be modified by substituting either the first or second D with an N, to arrive at SEQ ID NO:56 (HNAAIGYD) and SEQ ID NO:57 (HDAAIGYN), respectively.

Exemplary peptides that may have δPKC antagonistic activity that are derived from δPKC agonist peptides according to the methods of the present invention include those set forth in SEQ ID Nos: 58-65. These antagonists may be based on alternative ΨδRACK sequences described above and may be modified to form antagonists according to the present invention. For example, SEQ ID NO:4 (MRVAEEPV) may be modified by changing R to D or E to arrive at SEQ ID NO:58 (MDVAEEPV) and SEQ ID NO:59 (MEVAEEPV), respectively. Alternatively, the second E in SEQ ID NO:4 (MRVAEEPV) may be substituted with N or Q to arrive at SEQ ID NO:60 (MRVAENPV) and SEQ ID NO:61 (MRVAEQPV). Similar modifications can be made, for example, to SEQ ID NO:27 (MRLAEEPV) to arrive at SEQ ID NO:62 (MDLAEEPV) (changing R to D); SEQ ID NO:63 (MELAEEPV) (changing R to E); SEQ ID NO:64 (MRLAENPV) (changing the second E with N); and SEQ ID NO:65 (MRLAEQPV) (changing the second E to Q).

Exemplary peptides that may have ηPKC antagonistic activity that are derived from ηPKC agonist peptides according to the methods of the present invention include those set forth in SEQ ID Nos:66-69. These antagonists may be based on the ΨηRACK sequence described above as well as the alternative ΨηRACK sequences and may be modified to form antagonists according to the present invention. For example, SEQ ID NO:6 (HETPLGYD) and SEQ ID NO:34 (KETPAGYD) may be modified by substituting E for Q or N to arrive at SEQ ID NO:66 (HETPLGYD); SEQ ID NO:67 (KNTPAGYD); SEQ ID NO:68 (KQTPAGYD); and SEQ ID NO:69 (KNTPAGYD).

Exemplary peptides that may have θPKC antagonistic activity that are derived from θPKC agonist peptides according to the methods of the present invention include those set forth in SEQ ID Nos:70-78. These antagonists may be based on the ΨθRACK sequence described above as well as the alternative ΨθRACK sequences and may be modified to form antagonists according to the present invention. For example, SEQ ID NO:5 (KGKNVDLI) may be modified by substituting the second K with either D or E to arrive at SEQ ID NO:70 (KGDNVDLI) and SEQ ID NO:71 (KGENVDLI); substituting N for E to arrive at SEQ ID NO:72 (KGKEVDLI); or substituting D for N to arrive at SEQ ID NO:73 (KGKNVNLI); Similarly, SEQ ID NO:37 (RGKNVELA) may be modified by substituting K with either D or E to arrive at SEQ ID NO:74 (RGKNVELA) and SEQ ID NO:75 (RGENVELA), respectively. Additionally, SEQ ID NO:43 (KGKQVDLI) may be modified by substituting D for N to arrive at SEQ ID NO:76 (KGKQVNLI) or by substituting the second K with D or E to arrive at SEQ ID NO:77 (KGDQVNLI) and SEQ ID NO:78 (KGEQVNLI), respectively.

Exemplary peptides that may have βPKC antagonistic activity that are derived from βPKC agonist peptides according to the methods of the present invention include those set forth in SEQ ID Nos:79-85. These antagonists may be based on the ΨβRACK sequence described above as well as the alternative ΨβRACK sequences and may be modified to form antagonists according to the present invention. For example, SEQ ID NO:7 (SVEIWD), SEQ ID NO:45 (SAEIWD); SEQ ID NO:46 (SVELWD); SEQ ID NO:47 (TVEIWE); SEQ ID NO:48 (SVEIWE) and SEQ ID NO:49 (SVEIW) may all be modified by substituting E with K, to arrive at SEQ ID NO:80 (SVKIWD); SEQ ID NO:81 (SAKIWD); SEQ ID NO:82 (SVKLWD); SEQ ID NO:83 (TVKIWE); SEQ ID NO:84 (SVKIWE) and SEQ ID NO:85 (SVKIW).

It is understood that this is not an exhaustive list of the antagonists that may be produced by the various agonists described herein. Other similar PKC agonist sequences, or alternative ΨRACK sequences for the respective PKC isozymes described herein and/or otherwise known to the art, may be modified using the methods described herein to produce a PKC antagonist. It will also be appreciated from the description herein that the methodology extends beyond the specific substitutions described herein. Substitution of negatively charged or positively charged amino acid residues in a peptide with polar, uncharged amino acid residues is contemplated to effect a change in the activity of the peptide or peptidomimetic, as are substitutions of polar, uncharged amino acids with positively or negatively charged amino acids. Substitution of positively charged amino acids with negatively charged amino acids, and substitution of negatively charged amino acids with positively charged amino acids is also envisioned. Positively charged amino acids include lysine, arginine and histidine. Negatively-charged amino acids include aspartic acid and glutamic acid. Polar, uncharged amino acids that can substitute for selected amino acids include serine, threonine, cysteine, tyrosine, asparagine, and glutamine. The amino acids are expected to have the aforementioned charges at least at physiological pH (e.g., about pH 7). Accordingly, for example, lysine, arginine and histidine can be substituted with aspartic acid or glutamic acid. Aspartic acid and glutamic acid can be substituted with, for example, asparagine, glutamine, lysine or arginine. Serine and threonine can be substituted with, for example, glutamic acid, aspartic acid, glutamine or asparagine.

The PKC peptide agonists or antagonists described herein may be obtained by methods known to the skilled artisan. For example, the protein agonist and/or antagonist may be chemically synthesized using various solid phase synthetic technologies known to the art and as described in, for example, Williams, Paul Lloyd, et al. *Chemical Approaches to the Synthesis of Peptides and Proteins*, CRC Press, Boca Raton, Fla., (1997). Additionally, methods of converting a peptide into a peptidomimetic are also well known to the skilled artisan.

Alternatively, the protein agonist or antagonist may be produced by recombinant technology methods as known in the art and as described, for example, in Sambrook et al., *Molecular Cloning: A Laboratory Manual*, Cold Springs Harbor laboratory, $2^{nd}$ ed., Cold Springs Harbor, N.Y. (1989); Martin, Robin, *Protein Synthesis: Methods and Protocols*, Humana Press, Totowa, N.J. (1998); and *Current Protocols in Molecular Biology* (Ausubel et al., eds.), John Wiley & Sons, which is regularly and periodically updated. For example, an expression vector may be used to produce the desired peptide agonist or antagonist in an appropriate host cell and the product may then be isolated by known methods. The expression vector may include, for example, the nucleotide sequence encoding the desired peptide wherein the nucleotide sequence is operably linked to a promoter sequence.

As defined herein, a nucleotide sequence is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous. Additionally, as defined herein, a nucleotide sequence is intended to refer to a natural or synthetic linear and sequential array of nucleotides and/or nucleosides, and derivatives thereof. The terms "encoding" and "coding" refer to the process by which a nucleotide sequence, through the mechanisms of transcription and translation, provides the information to a cell from which a series of amino acids can be assembled into a specific amino acid sequence to produce a polypeptide.

The agonists or antagonists may include natural amino acids, such as the L-amino acids or non-natural amino acids, such as D-amino acids. The amino acids in the peptide may be linked by peptide bonds or, in modified peptides, including peptidomimetics described herein, by non-peptide bonds.

A wide variety of modifications to the amide bonds which link amino acids may be made and are known in the art. Such modifications are discussed in general reviews, including in Freidinger, R. M. "Design and Synthesis of Novel Bioactive Peptides and Peptidomimetics" *J. Med. Chem.* 46:5553 (2003), and Ripka, A. S., Rich, D. H. "Peptidomimetic Design" *Curr. Opin. Chem. Biol.* 2:441 (1998). These modifications are designed to improve the properties of the peptide in one of two ways: (a) increase the potency of the peptide by restricting conformational flexibility; (b) increase the half-life of the peptide by introducing non-degradable moieties to the peptide chain.

Examples of strategy (a) include the placement of additional alkyl groups on the nitrogen or alpha-carbon of the amide bond, such as the peptoid strategy of Zuckerman et al, and the alpha modifications of, for example Goodman, M. et. al. [*Pure Appl. Chem.* 68:1303 (1996)]. The amide nitrogen and alpha carbon may be linked together to provide additional constraint [Scott et al, *Org. Letts.* 6:1629-1632 (2004)].

Examples of strategy (b) include replacement of the amide bond by, for instance, a urea residue [Patil et al, *J. Org. Chem.* 68:7274-7280 (2003)] or an aza-peptide link [Zega and Urleb, *Acta Chim. Slov.* 49:649-662 (2002)]. Other examples such as introducing an additional carbon ["beta peptides", Gellman, S. H. *Acc. Chem. Res.* 31:173 (1998)] or ethene unit [Hagihara et al, *J. Am. Chem. Soc.* 114:6568 (1992)] to the chain, or the use of hydroxyethylene moieties [Patani, G. A., Lavoie, E. J. *Chem. Rev.* 96:3147-3176 (1996)] are also well known. One or more amino acids may be replaced by an isosteric moiety such as, for example, the pyrrolinones of Hirschmann et al [*J. Am. Chem. Soc.* 122:11037 (2000)], or tetrahydropyrans [Kulesza, A. et al., *Org. Letts.* 5:1163 (2003)].

In yet another aspect of the invention, methods of modulating the activity of a PKC enzyme, such as εPKC, by administering in vitro or in vivo a PKC antagonist are provided. The PKC antagonist can be a peptide, i.e., an amino acid sequence, or a peptidomimetic organic molecule selected to simulate the action of the peptide. As an example, methods of inhibiting the activity of a protein kinase C (PKC) enzyme are provided. In one form, a method includes contacting a PKC enzyme with a PKC inhibitor peptide or peptidomimetic, wherein the peptide or peptidomimetic is derived from a PKC agonist peptide or peptidomimetic and wherein at least one amino acid in the agonist peptide or peptidomimetic is substituted with another amino acid sufficient to convert the agonist peptide or peptidomimetic into an antagonist peptide or peptidomimetic. The agonist peptides suitable for use are as previously described herein. The amino acid substitutions amenable to convert the agonist peptide or peptidomimetic into an antagonist peptide or peptidomimetic are also previously described herein.

In yet another aspect of the invention, methods of treating conditions modulated by a PKC enzyme are provided. In one form, a method includes administering to a patient in need thereof a therapeutically effective amount of a peptide, or peptidomimetic, that acts as an antagonistic modulator of a corresponding PKC isozyme. One PKC antagonist, or a combination of PKC antagonists, may be administered. Such antagonists are those previously described herein.

A wide variety of diseases or conditions may be treated that are modulated by PKC. The diseases or conditions that are treated herein are typically those which are associated with increased activity of the respective PKC isozyme and that would benefit from administration of a PKC antagonist. As one example, various inflammatory diseases and fibrotic diseases have been associated with an increased activity of εPKC [Aksoy, E., et al., *Int. J. Biochem. Cell. Biol.* 36:183-188 (2004); Fang, Q. et al., *Eur. Respir. J.* 24:918-924 (2004)]

Accordingly, conditions amenable for treatment with an εPKC antagonist include, for example, fibrotic diseases, including pulmonary fibrosis, and scleroderma; and inflammatory diseases, including, for example, inflammatory bowel disease, septic shock, allergic rhinitis; lung diseases, including chronic obstructive pulmonary disease, and asthma; autoimmune diseases, including multiple sclerosis, Guillain-Barre syndrome, psoriasis, Grave's disease, rheumatoid arthritis and immune-mediated diabetes, including Type 1 diabetes mellitus.

The inhibitors described herein may be modified by being part of a fusion protein. The fusion protein may include a protein or peptide that functions to increase the cellular uptake of the peptide inhibitors, has another desired biological effect, such as a therapeutic effect, or may have both of these functions. For example, it may be desirable to conjugate, or otherwise attach, an εPKC or other peptide or peptidomimetic antagonist to a cytokine or other protein that elicits a desired biological response. The fusion protein may be produced by methods known to the skilled artisan. The inhibitor peptide may be bound, or otherwise conjugated, to another peptide in a variety of ways known to the art. For example, the inhibitor peptide or peptidomimetic may be bound to a carrier peptide or other peptide described herein via cross-linking wherein both peptides of the fusion protein retain their activity. As a further example, the peptides may be linked or otherwise conjugated to each other by an amide bond from the C-terminal of one peptide to the N-terminal of the other peptide. The linkage between the inhibitor peptide and the other member of the fusion protein may be non-cleavable, with a peptide bond, or cleavable with, for example, an ester or other cleavable bond known to the art.

Furthermore, in other forms of the invention, the carrier protein or peptide that may increase cellular uptake of the peptide antagonist may be, for example, a *Drosophila* Antennapedia homeodomain-derived sequence which is set forth in SEQ ID NO:91 (CRQIKIWFQNRRMKWKK), and may be attached to the inhibitor by cross-linking via an N-terminal Cys-Cys bond as discussed in Theodore, L., et al. *J. Neurosci.* 15:7158-7167 (1995); Johnson, J. A., et al. *Circ. Res* 79:1086 (1996). Alternatively, the inhibitor may be modified by a Transactivating Regulatory Protein (Tat)-derived transport polypeptide (such as from amino acids 47-57 of Tat shown in SEQ ID NO:92; YGRKKRRQRRR) from the Human Immunodeficiency Virus, Type 1, as described in Vives, et al., *J. Biol. Chem*, 272:16010-16017 (1997), U.S. Pat. No. 5,804,604 and Genbank Accession No. AAT48070; or with polyarginine as described in Mitchell, et al. *J. Peptide Res.* 56:318-325 (2000) and Rolhbard, et al., *Nature Med.* 6:1253-1257 (2000). The inhibitors may be modified by other methods known to the skilled artisan in order to increase the cellular uptake of the inhibitors.

The inhibitors may be advantageously administered in various forms. For example, the inhibitors may be administered in tablet form for sublingual administration, in a solution or emulsion. The inhibitors may also be mixed with a pharmaceutically-acceptable carrier or vehicle. The carrier may be a liquid, suitable, for example, for parenteral administration, including water, saline or other aqueous solution, or may be an oil. The carrier may be selected for intravenous or intraarterial administration, and may include a sterile aqueous or non-aqueous solution that may include preservatives, bacteriostats, buffers and antioxidants known to the art. In tablet form, a solid carrier may include, for example, lactose, starch, carboxymethyl cellulose, dextrin, calcium phosphate, calcium carbonate, synthetic or natural calcium allocate, magnesium oxide, dry aluminum hydroxide, magnesium stearate, sodium bicarbonate, dry yeast or a combination thereof. The tablet preferably includes one or more agents which aid in oral dissolution. The inhibitors may also be administered in forms in which other similar drugs known in the art are administered.

The inhibitors may be administered to a patient by a variety of routes. For example, the inhibitors may be administered parenterally, including intraperitoneally, intravenously, intraarterially, subcutaneously, or intramuscularly. The inhibitors may also be administered via a mucosal surface, including rectally, and intravaginally; intranasally, including by inhalation; sublingually; intraocularly and transdermally. Combinations of these routes of administration are also envisioned.

A therapeutically effective amount of the εPKC or other inhibitor peptide is provided. As used herein, a therapeutically effective amount of the inhibitor is the quantity of the inhibitor required to decrease or eliminate the symptoms associated with a particular disease or condition. Such clinical endpoints are well known in the art for a wide variety of diseases or conditions. This amount includes the amount which is effective in modulating, such as decreasing, the activity of the respective PKC enzyme. For example, the therapeutically effective amount includes an amount effective in affecting the intracellular activity of the PKC enzyme, including kinase activity, PKC enzyme translocation activity and/or otherwise preventing PKC from performing its biological function. This amount will vary depending on the route of administration, the duration of treatment, the specific inhibitor used, the particular disease or condition and the health of the patient as known in the art. The skilled artisan will be able to determine the optimum dosage. Generally, the amount of inhibitor typically utilized may be, for example, about 0.0005 mg/kg body weight to about 20 mg/kg body weight, but is preferably about 0.001 mg/kg to about 5 mg/kg.

The patient to be treated is typically one in need of such treatment, including one that is affected by a particular disease or condition amenable to treatment with a PKC antagonist. The patient is furthermore typically a vertebrate, preferably a mammal, and including a human. Other animals which may be treated include farm animals, such as horse, sheep, cattle, and pigs. Other exemplary animals that may be treated include cats, dogs; rodents, including those from the order Rodentia, such as mice, rats, gerbils, hamsters, and guinea pigs; members of the order Lagomorpha, including rabbits and hares, and any other mammal that may benefit from such treatment. The patient is preferably treated in vivo.

Thus, the PKC peptide antagonists, including the εPKC antagonists, described herein find use as therapeutic agents for treatment of conditions involving translocation or other activity of εPKC. Administration of the PCK antagonist will, for example, inhibit translocation and the subsequent cascade of signaling events. The antagonist also finds use in studies on the effect of PKC isozymes in ischemia and other conditions, and can also be used as a screening aid in designing therapeutic agents with antagonistic activity or that act as mimics of the peptide.

Reference will now be made to specific examples illustrating the invention described above. It is to be understood that the examples are provided to illustrate preferred embodiments and that no limitation to the scope of the invention is intended thereby. Additionally, all documents cited herein are indicative of the level of skill in the art and are hereby incorporated by reference in their entirety.

EXAMPLE 1

Effect of N-ΨεRACK on Cardiac Myocytes

A. Peptide Preparation and Delivery to Cells

The following peptides were synthesized and purified (>95%) by conventional techniques:

```
ψεRACK
(SEQ ID NO: 3, HDAPIGYD, εPKC amino acid
residues 85-92);

N-ψεRACK
(SEQ ID NO: 55, HNAPIGYD);

A-ψεRACK
(SEQ ID NO: 79, HAAPIGYD);

εV1-2
(SEQ ID NO: 86, EAVSLKPT; εPKC amino acid
residues 14-21 and described in
U.S. Pat. No. 6,165,977);

ψβRACK
(SEQ ID NO: 7, SVEIWD, βPKC
amino acids 241-246).
```

The peptides were either unmodified or were cross-linked via an N-terminal Cys-Cys bond to the Drosophila Antennapedia homeodomain-derived carrier peptide (SEQ ID NO:6, C-RQIKIWFQNRRMKWKK) (Derossi, D., et al., *J. Biol. Chem.* 269:10444-10450, (1994); Derossi, D., et al., *J. Biol. Chem.* 271:18188-18193, (1996); Théodore, L., et al., *J. Neurosci.* 15:7158-7167, (1995)). This carrier peptide (SEQ ID NO:6) was used as a control peptide.

Primary cardiac myocyte cell cultures (90-95% pure) were prepared from newborn rats as previously described (Gray, M. O., et al., *J. Biol. Chem.* 272:30945-30951, (1997); Disatnik, M.-H., et al., *Exp. Cell Res.* 210:287-297, (1994)). Peptides (100 nM-1 μM applied concentration) were introduced into cells by transient permeabilization (Johnson, J. A., et al., *Circ. Res.* 79:1086-1099, (1996)) with sham permeabilization as control, or as carrier-peptide conjugates (30 nM-1 μM) (Derossi, D. et al., surpa (1994); Derossi, D. et al., surpa (1996); Théodore, L., et al., surpa (1995)) with a carrier-carrier dimer as a control.

Cells were treated for 10-20 minutes in the absence or presence of peptide followed by an additional incubation with or without 1 nM phorbol 12-myristate 13-acetate (PMA) for 10 or 20 minutes. Alternatively, cells were incubated for 10 minutes with 100 nM PMA (positive control) or in the absence of PMA.

B. Cardiac Myocyte Contraction Rate Measurement

Measurements of cardiac myocyte contraction rate were carried out essentially as previously described (Johnson, J. A., et al., *J. Biol. Chem.* 271:24962-24966, (1996). In brief, cardiomyocytes cultured on 35 mm plates were placed in a temperature-regulation apparatus at 37° C. (Medical Systems Corp.) and positioned on the stage of an inverted microscope (Carl Zeiss Inc.). The contraction rates of four cells in one microscopic field were determined every 2 minutes for 15 seconds each. The basal contraction rate (~300 beats/minute) was stable over many hours.

Results

As described above, the peptides represented by SEQ ID NOs:1-5 were synthesized and purified. Specifically, ΨεRACK (SEQ ID NO:3, HDAPIGYD), N-ΨεRACK (SEQ ID NO:55, HNAPIGYD), A-ΨεRACK (SEQ ID NO:79, H AAPIGYD); εV1-2 (SEQ ID NO:86, EAVSLKPT); and ΨβRACK (SEQ ID NO:7, SVEIWD) were prepared. The peptides were either unmodified or were cross-linked via an N-terminal Cys-Cys bond to the Drosophila Antennapedia homeodomain-derived carrier peptide (SEQ ID NO:81, C-RQIKIWFQNRRMKWKK).

Peptide SEQ ID Nos:3, 55 and 79 were introduced into cardiac myocyte cell cultures prepared from newborn rats by transient permeabilization, with sham permeabilization as control, or as carrier-peptide conjugates with a carrier-carrier dimer as control. The cells were treated for 10-20 minutes in the absence or presence of peptide followed by an additional incubation with or without phorbol 12-myristate 13-acetate (PMA) for 10 or 20 minutes. Alternatively, cells were incubated for 10 minutes with 100 nM PMA (positive control) or in the absence of PMA. The effect of the peptide and/or PMA was determined by measuring the contraction rate of the myocytes, as described in Example 1B.

Figure 1A:
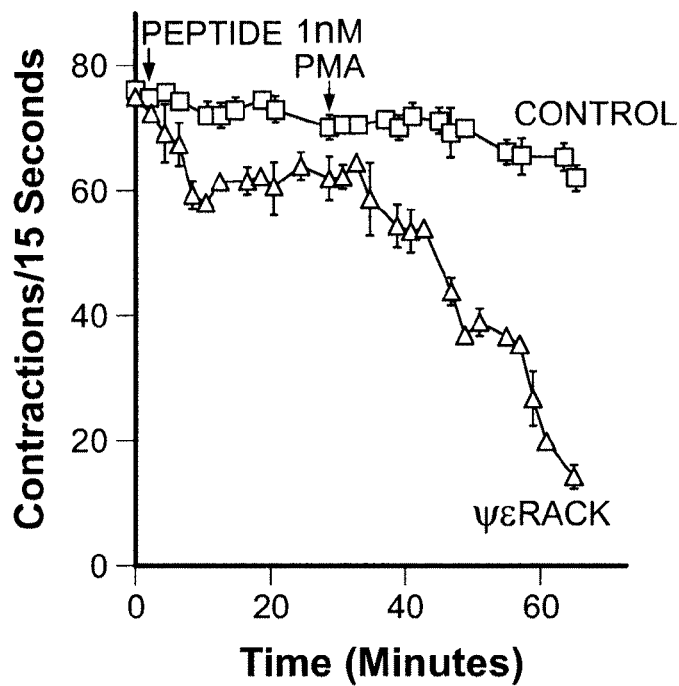
FIG. 1A is a graph showing the number of contractions measured in a 15 second interval in neonatal rat cardiac myocytes as a function of time in cells treated with a control, carrier peptide (squares) and in cells treated with ΨεRACK peptide (triangles), where both cell populations (control and ΨεRACK peptide treated) were treated with phorbol 12-myristate 13-acetate (PMA) at 30 minutes as more fully described in Example 1.

FIG. 1A shows the results for cells treated with ΨεRACK (triangles) and for cells treated with a control peptide (squares), followed by incubation with PMA which was added to the culture about 30 minutes after initiation of the experiment (addition of PMA is indicated by the arrows on graph in FIG. 1A). About 10 minutes after ΨεRACK peptide application to the cells, a reduction in the contraction rate of cardiomyocytes was induced, as compared to the control cells. The reduction observed in the presence of ΨεRACK was greatly enhanced by the addition of PMA, which is known to induce reduction in the contraction rate of cardiac myocytes (Johnson, J. A. et al., *J. Biol. Chem.*, 271:24962 (1996)).

Figure 1B:
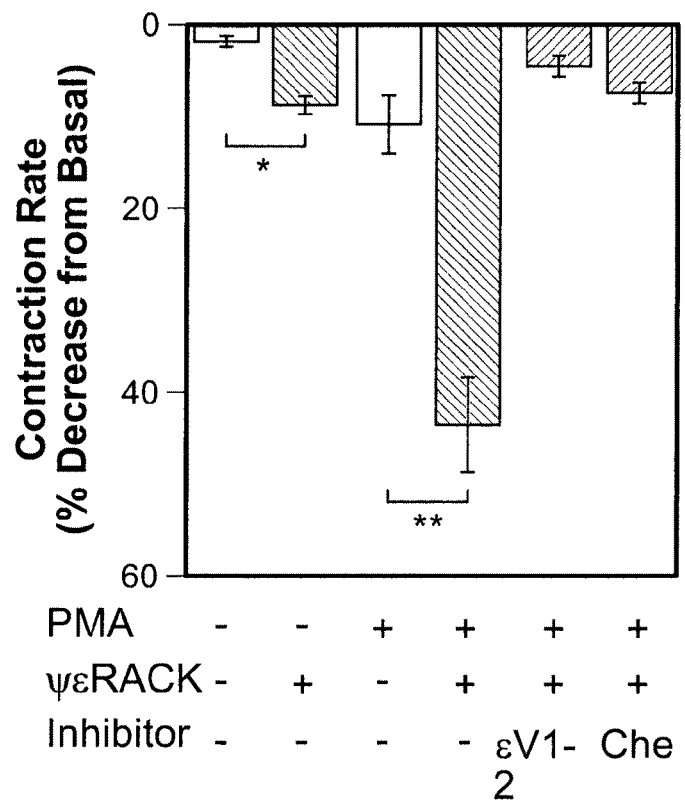
FIG. 1B is a bar graph showing the contraction rate of neonatal rat cardiac myocytes, expressed as the percent decrease in contraction rate relative to the basal contraction rate, after treatment with (i) the εPKC agonist peptide (Ψε-RACK peptide), (ii) phorbol 12-myristate 13-acetate (PMA), (iii) PMA and ΨεRACK peptide, (iv) PMA, ΨεRACK peptide, and εV1-2 peptide, or (v) PMA, ΨεRACK peptide, and chelerythrine (Che) as more fully described in Example 1.

FIG. 1B shows the percent decrease in contraction rate of neonatal rat cardiac myocytes, where the percent decrease is relative to the basal contraction rate of the cells which spontaneously and stably beat at about 300 beats per minute. Cells treated with ΨεRACK peptide had a 9±2% decrease in contraction rate from the basal rate for ΨεRACK, 20 minutes after peptide addition, as compared to 2±1% for cells treated with a control peptide. Cells treated with ΨεRACK together with PMA experienced a decrease of 44±6% from the basal contraction rate, whereas treatment with PMA alone caused a decrease of only 11±4%.

With continuing reference to FIG. 1B, cells were also treated with an εPKC-specific inhibitor peptide, εV1-2, to determine whether the ΨεRACK effect on contraction rate was due to its ability to induce εPKC translocation, since, if this is the case, then an εPKC-selective translocation inhibitor should inhibit translocation. Indeed, the ΨεRACK effect on contraction of cardiac myocytes was abolished by prior application of the εPKC-specific inhibitor peptide εV1-2, as seen in FIG. 1B. In addition, if the ΨεRACK effect is due to an increase in the catalytic activity of εPKC, this effect should be abolished by an inhibitor of the catalytic activity. As seen, the non-selective PKC inhibitor chelerythrine (Che) inhibited ΨεRACK-induced negative chronotropy. These data demonstrate that εPKC activation is required and sufficient to induce negative chronotropy in neonatal cardiac myocytes.

The results in FIG. 1A-1B establish that ΨεRACK stimulates suppression of the contraction rate in cardiac myocytes. The methodology provides a means to determine the effect of other peptides and peptidomimetics on translocation of εPKC. Thus, a peptide having the sequence HNAPIGYD (SEQ ID NO:55) was designed, which is referred to herein as N-ΨεRACK as the sequence is identical to ΨεRACK (HDAPIGYD, SEQ ID NO:3) except for substitution of aspartate (D), a negatively charged amino acid, to asparagine (N), a polar, uncharged amino acid. The effect of N-ΨεRACK on the contraction rate of cardiac myocytes was studied and the results are shown in FIGS. 2A-2C.

FIG. 2A shows the contraction rate of neonatal rat cardiac myocytes as a function of time after treatment with a control peptide (squares) or with N-ΨεRACK (diamonds). The contraction rate is expressed as the percent decrease in contraction rate relative to the basal contraction rate, discussed above and in Example 1. In contrast to ΨεRACK, N-ΨεRACK had no agonistic effect on contraction rate of cardiac myocytes as seen by the fact that the contraction rate of the cells treated with N-ΨεRACK was approximately the same as the cells treated with a control peptide, during the first 20 minutes of the data presented in FIGS. 2A-2B, prior to PMA treatment. The cells were treated with PMA about 20 minutes after peptide treatment, and as seen in FIGS. 2A-2B at times greater than about 20 minutes, N-ΨεRACK acted as an antagonist of εPKC. That is, N-ΨεRACK was able to reduce the decrease in contraction rate induced by PMA. As seen in FIG. 2B, ΨεRACK reduced the decrease in contraction rate induced by 5 nM PMA. In a study not shown here, N-ΨεRACK reduced the decrease in contraction rate induced by 10 nM PMA from 47±3% to 24±5% 40 minutes after PMA addition (n=4; p<0.05).

FIG. 2C shows the percent decrease in contraction rate for cardiac myocytes treated with N-ΨεRACK (diamonds). About 15 minutes after treatment with N-ΨεRACK, the cells were additionally treated with ΨεRACK, as indicated by the arrows at the 15 minute time point. Control cells, treated with ΨεRACK at the 15 minutes time point (triangles), showed an immediate decrease in contraction rate; however the cells treated with both N-ΨεRACK and ΨεRACK had little change in contraction rate. Treatment of the cells with PMA at the 30 minute time point led to a further decrease in contraction rate in the control cells not treated with N-ΨεRACK. However, cells treated with N-ΨεRACK had less than a 10% decrease in contraction rate, indicating the N-ΨεRACK was able to almost completely abolish the combined effect of ΨεRACK and PMA in decreasing the contraction rate. Thus, N-ΨεRACK acts as an antagonist of εPKC function in cardiac myocytes.

Although not being limited by theory, it is contemplated that both ΨεRACK and N-ΨεRACK bind to the RACK-binding site in εPKC. The ΨεRACK acts by reversibly interfering with the intramolecular interaction between the RACK binding site and the ΨεRACK sequence, whereas N-ΨεRACK acts by interfering with the intermolecular interaction between the RACK binding site and εRACK. It is also possible that the peptides affect access of the enzyme to its substrate or post-translational modifications of εPKC such as phosphorylation; phosphorylation modulates activation and translocation of the conventional PKC isozymes. In the examples described herein, a charged amino acid was substituted with an uncharged amino acid to arrive at a peptide that more closely resembled an endogenous anchoring protein. The sequence of a cognate receptor for any sequence provides guidance in ascertaining the substitution.

EXAMPLE 2

Effect of N-ΨεRACK on Translocation of εPKC

Figure 3A:
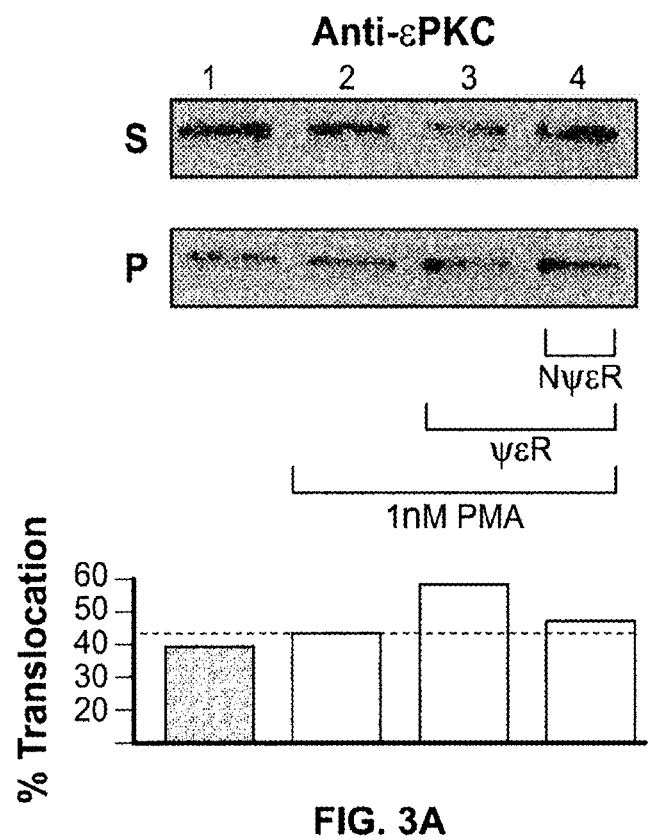
FIGS. 3A-3B shows Western blot analysis of PMA-induced translocation of εPKC (FIG. 3A) and αPKC (FIG. 3B)
Figure 3B:
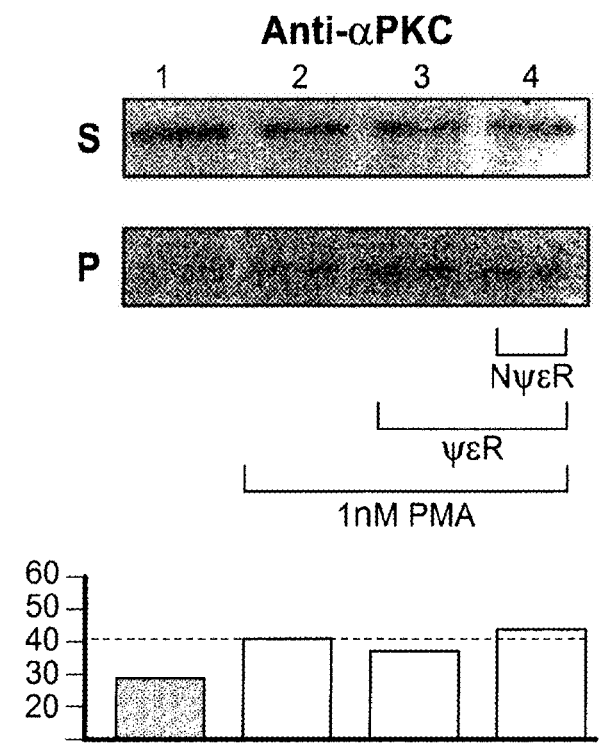

Translocation of specific PKC isozymes in rat neonatal and adult cardiac myocytes was assessed after peptide treatment by using PKC isozyme-specific antibodies in western blot analysis (Santa Cruz Biotechnology, Inc.) of cytosolic and particulate fractions of treated cells, as previously described (Johnson, J. A. and Mochly-Rosen, D., *Circ. Res.* 76:654-663, (1995)). In brief, after peptide treatment the cells were homogenized, fractionated, and analyzed by Western blot. Blots were first probed with anti-εPKC (FIG. 3A), followed by stripping and re-probing for anti-αPKC (FIG. 3B). Percent translocation (amount of PKC in the particulate fraction over total amount of PKC in the cell) is shown in the histograms of FIGS. 3A-3B.

Results

Western blot analysis was used to evaluate the translocation of εPKC from cytosolic to particulate subcellular fractions, a hallmark of PKC activation. N-ΨεRACK or ΨεRACK peptides were introduced into the cells by transient permeabilization in the presence of a dose of PMA (1 nM). As described in Example 2, the cells were then homogenized, fractionated, and analyzed by Western blot. Blots were first probed with anti-εPKC, and is shown in FIG. 3A. The blots were then stripped and reprobed with anti-αPKC, as shown in FIG. 3B. The percent translocation is shown in the histogram in FIGS. 3A-3B, taken as amount of PKC in the particulate fraction over total amount of PKC in the cell. The Western blot shows that N-ΨεRACK inhibited PMA-induced translocation and is, therefore, an antagonist of PMA and ΨεRACK-induced εPKC translocation, and of εPKC function (FIG. 2).

EXAMPLE 3

Effect of N-ΨεRACK on ΨεRACK-Inducted Protection from Ischemia

Cardiac myocytes were isolated from adult male rats as previously described (Chen et al., *Proc. Natl. Acad. Sci.*, 96(22):12784 (1999)). Myocytes in incubation buffer were treated with a peptide or combination of peptides, prepared as described in Example 1, for 15 minutes. Myocytes were then pelleted at 1000 rpm for 1 minute in a degassed incubation buffer saturated with nitrogen and incubated at 37° C. for 3 hours to simulate ischemia. Cell damage was assessed after the 3 hours by trypan blue exclusion and percent cell with damage was determined as previously described (Chen et al., *Proc. Natl. Acad. Sci.*, 96(22):12784 (1999)).

Results

ΨεRACK (SEQ ID NO:1) when administered to cells confers protection against ischemia (Dorn et al., *Proc. Natl. Acad. Sci.*, 96(22):12798 (1999)). In this example, the effect of N-ΨεRACK on cells exposed to an ischemic episode was evaluated. Additionally, a peptide having the sequence H AAPIGYD (SEQ ID NO:3), referred to as A-ΨεRACK, was prepared to determine the effect of changing the aspartate (D) residue in ΨεRACK (HDAPIGYD; SEQ ID NO:3), since, if this residue is important for the action of the peptide as an agonist, its substitution to alanine (A), an uncharged, nonpolar amino acid, should render the peptide inactive. The effect of this peptide on cardiac protection was also evaluated. As described in this example, cardiac myocytes were treated with ΨεRACK, N-ΨεRACK, A-ΨεRACK, εV1-2 peptides and various combinations of these peptides before simulated ischemia. After a simulated ischemic episode, the cell damage was evaluated by trypan blue dye exclusion. The results are shown in FIG. 4.

FIG. 4 is a bar graph showing the percentage of cell damage to rat cardiac myocytes resulting from an ischemic episode, where myocytes not subjected to ischemia are represented by the clear area in each bar, and the percent of ischemic damage represented by the filled area. As a control for PKC activity, myocytes were treated with a combination of chelerythrine (Che) and ΨεRACK peptide. Treatment with ΨεRACK peptide reduced ischemia-induced cell damage by 60%. However, N-ΨεRACK and A-ΨεRACK had no effect on response to ischemia, indicating that a change of aspartate to asparagine or alanine results in loss of agonist activity of ΨεRACK. Moreover, a combination of N-ΨεRACK and ΨεRACK abolished protection from ischemic damage. Inhibition of εPKC with its selective inhibitor εV1-2 or with an inhibitor of PKC catalytic activity, Che, reversed ΨεRACK-induced protective effect. N-ΨεRACK abolished ΨεRACK-induced protection, whereas the inactive peptide, A-Ψε-RACK did not, indicating that N-ΨεRACK is an εPKC inhibitor.

These findings show that a single amino acid substitution, increasing the resemblance of ΨεRACK to the εRACK sequence resulted in a loss of the agonist activity and a gain of antagonist activity. The ΨεRACK peptide agonist interferes with the intramolecular interaction in PKC, without altering the intermolecular interaction of PKC with its RACK or with lipids. In addition, this peptide exposes at least part of the RACK-binding site on εPKC, and is then displaced by εRACK to obtain full activation. In contrast, the N-ΨεRACK peptide interferes not only with the intramolecular interaction between the RACK-binding site and ΨεRACK, but also with the intermolecular interaction between εPKC and εRACK. Since the interaction between εPKC and εRACK is inhibited, translocation and εPKC function is consequently also inhibited.

EXAMPLE 4

Sensitivity to Protease Degradation of the Different ΨεRACK εPKC Mutants

If the D86 in the ΨεRACK site is engaged in an intramolecular interaction with the RACK-binding site, the D(86)N mutant may reside more in the closed state, and therefore be more resistant to proteolysis. In contrast, the D(86)A mutant should favor an open conformation and therefore be more susceptible to proteolysis. To test this hypothesis, εPKC Wt and mutants expressed in insect cells were subjected to proteolysis by the endopeptidase, Arg C, as previously shown for εPKC [Orr, J. W. et al., *J. Biol. Chem.* 267:15263-15266 (1992)]. Degradation by Arg C was monitored by the decrease of full-length εPKC.

Materials

Restriction enzymes were from New England Biolabs. Anti-εPKC V5 antibodies were from Santa Cruz Biotechnology.

Cell Cultures

CHO-Hir cells (kindly provided by BioImage A/S, Soeborg, Denmark) were kept in culture in F-12(HAM) nutrient mixture supplemented with glutamax (Gibco-Brl), 10% fetal bovine serum (US qualified, Gibco-Brl) and antibiotics (100 units/ml penicillin and 100 µg/ml Streptomycin sulfate, Gibco-Brl). MCF7 cells (a gift of James Ford, Stanford University) were kept in RPMI1640 media (Gibco-Brl) supplemented with 5% FBS and antibiotics. Cells were cultured at 37° C. 5% CO2. Insect cells were grown at 26° C., Sf9 cells were cultured in SF900II SFM media (Gibco-Brl) supplemented with 10% fetal bovine serum (Gibco-Brl), and antibiotics. Hi5 insect cells were cultured in Insect Xpress (Bio Whittaker) containing antibiotics.

Constructs

The EGFP-εPKC construct used in these studies was kindly provided by BioImage A/S, Soeborg, Denmark. This construct contained two amino acid substitutions [Q(34)A and S(336)G], when compared to the human εPKC sequence deposited in the gene bank, accession number X65293. Site-directed mutagenesis of this clone was performed using the Quick Change site directed mutagenesis kit (Stratagene) according to the manufactures instructions. Primers used for the site directed mutagenesis were: for D(86)N forward primer (5'-GTAGCCTATGGGGGCATTGTGAAAGA-CAGCCAG-3') (SEQ ID NO:87) and reverse primer (5'-CTGGCTGTCTTTCACAATGCCCCCATAGGC TAC-3') (SEQ ID NO:88). For D(86)A forward primer (5'-CTGGCT-GTCTTTCACGCTGCCCCCATAGGCTAC) (SEQ ID NO:89) and reverse primer. (5'-GTAGC-CTATGGGGGCAGCGTGAAA GACAGCCAG-3') (SEQ ID NO:90). The εPKC mutants were fully sequenced and subcloned by cutting and re-ligating into the XhoI and BamHI (New England Biolabs) sites into pEYFPC1 and pECFP C1 (Clontech). For expression in the baculovirus expression system GFP-εPKC was cut with XhoI and BamHI to release the insert, filled in with Klenow (New England Biolabs) and cloned into pvL1392 (BD Biosciences) digested with Sma1 (New England Biolabs). Human εRACK construct cloned into PZeoSV used in these studies was kindly provided by BioImage A/S, Soeborg, Denmark. The εRACK insert was released by cutting with ScaI (New England Biolabs) and XhoI, blunt ended with Klenow, and religated into the Sma1 site of PacG3X (BD Biosciences). εRACK was expressed as a GST fusion protein.

Transient Transfection:

Transfections of CHO-Hir, MCF-7 and Hi5 cells was carried out using FUGENE 6 (Roche) according to the manufacturers instruction.

Insect Cell Protein Expression

Baculovirus was produced in Sf9 cells and all proteins were expressed in Hi5 cells. Expression of all constructs was optimal at 72 h post-transfection. Infected Hi5 cells were lysed in homogenization buffer [20 mM Tris-HCl pH 7.5, 2 mM EDTA, 10 mM EGTA, 0.25 M sucrose, 12 mM βME, and protease inhibitors: leupeptin (25 µg/ml), aprotinin (25 µg/ml), PMSF (17 µg/ml), SBTI (20 µg/ml), E64 (25 µg/ml) (Sigma)]. The soluble fraction was isolated after a 30-minute spin at 49000 g and the supernatant was stored in 50% glycerol at −20° C. until further use Arg C Proteolysis Assay ArgC digests were performed as described [Orr, J. W. et al., J. Biol. Chem. 267:15263-15266 (1992)]. Crude insect cell lysate containing approximately 70 ng of PKC [determined by Western Blot comparison with standardized (PKC (PanVera)] was digested in 520 µl of 20 mM Tris pH 7.4 with 20 µl of endoproteinase ArgC (Boehringer Mannheim 25 units/ml) at room temperature. Aliquots were removed at the indicated time points run on 8% SDS-PAGE gels, followed by Western blot using anti-εPKC antibodies.

Statistical Analysis

For quantitative analysis autoradiographs were scanned and quantified using NIH image software. Analysis of fluorescence data was performed using MetaMorph® (Universal Imaging Corporation). To determine statistical significance a1 tail type 2 T-test (Microsoft excel) was used. Significance of time course curves was determined using two way ANOVA test (Stat View®).

Results

Although under these experimental conditions D(86)A mutation did not alter susceptibility of the enzyme to degradation by Arg C when compared to the wild type (Wt) enzyme, the D(86)N mutant was significantly more resistant to proteolysis than either D(86)A or Wt (FIG. 5A, B).

EXAMPLE 5

Binding of the εPKC Mutants to εRACK

RACKs bind active PKC [Mochly-Rosen, D. & Gordon, A. S., FASEB J. 12:35-42 (1998); Mochly-Rosen, D. et al., Molec. Biol. Cell. (formerly Cell Regulation) 1:693-706 (1990). If the intramolecular interaction between ΨεRACK and the RACK-binding site stabilizes the inactive closed form, increasing or decreasing the affinity of this intramolecular interaction should cause a corresponding decrease or increase in the ability of the enzyme to bind to its RACK. To test whether increasing or decreasing the affinity of the intramolecular interaction between ΨεRACK and the RACK-binding site proposed herein to stabilize the inactive closed form will cause a decrease or increase in the ability of the enzyme to bind its RACK, the binding of insect cell-expressed εPKC (Wt and ΨεRACK mutants) to immobilized GST-εRACK in the presence and absence of phospholipid (PL) activators was determined.

εRACK Binding Assay

Insect cells expressing either εPKC or GST-εRACK were lysed as described in Example 4. GST-εRACK, 0 1ng was immobilized on Glutathion-Sepharose 4B beads (Amersham-Pharmacia), and washed thoroughly with wash buffer (20 mM Tris-HCl pH 7.5, 2 mM EDTA, 100 mM NaCl, 12 mM βME, and 0.1% TritonX-100). Immobilized GST-εRACK was then incubated with the soluble fraction of insect cell lysates containing 100 ng Wt, D(86)A, or D(86)N εPKC protein, in the presence or absence of phospholipid activators (PL) (phosphatidylserine 12 µg/reaction and, Sn-1,2 dioleoylglycerol 400 ng/reaction) for 1 hour at 4° C. Upon thorough washing with wash buffer, bound proteins were eluted in SDS-PAGE sample buffer and proteins separated on 8% SDS-PAGE gels. The amount of εPKC interacting with εRACK was determined by Western blot probing for εPKC with anti εPKC-V5 antibodies. Blots were then re-probed with ant-GST (Santa Cruz) to verify that the same amount of GST-εRACK was present in each binding assay. All other methods for this Example were performed as described, for example, in Example 4.

Results

Binding of D(86)A εPKC mutant to εRACK in the absence of PL activators was at least two fold greater than binding of either D(86)N or Wt enzymes (FIG. 5C, D). Binding of D(86)N and of Wt enzyme to εRACK was significantly increased in the presence of PL, whereas binding of the D(86)A mutant to εRACK was not increased (FIG. 5C, D). In the presence of an equal concentration of PL, there was less εRACK binding of D(86)N εPKC than either D(86)A or Wt εPKCs. These results are consistent with the prediction that the εRACK-binding site in the D(86)A mutant is already available for binding to εRACK, whereas this site is masked in both Wt or D(86)N εPKCs and becomes accessible for binding only upon activation.

EXAMPLE 6

Rate of Translocation of εPKC and εPKC Mutants in Cells

The in vitro studies of ΨεRACK mutants and Wt εPKC described herein support the hypothesis proposed herein that ΨεRACK is involved in an intramolecular interaction that stabilizes the inactive closed state. To further test this hypothesis, the rate of translocation of ΨεRACK mutants and Wt εPKC in cells in response to stimulation was examined. It was hypothesized herein that part of the process of translocation requires disruption of the intramolecular interaction between the ΨεRACK site and the εRACK binding site. To investigate whether modulation of this intramolecular interaction could affect translocation rates of εPKC, εPKC ΨεRACK mutants were fused at their amino-termini to GFP, CFP or YFP proteins and translocation was analyzed both by cell fractionation and by real-time imaging.

Kinase Assay

The ability of the different εPKC mutants to phosphorylate substrates was assayed by following the incorporation of [$\gamma^{32}$P]ATP into myelin basic protein according to a method modified from Kikkawa, U. et al., *Biochem. Biophys. Res. Commun.* 135:636-643 (1986). Myelin basic protein phosphorylation was measured either by liquid scintillation or for immunoprecipitation experiments, by autoradiography. For kinase reaction of immunoprecipitated enzyme, beads were resuspended in 20 μl of a kinase reaction buffer composed of 20 mM Tris pH 7.5, [[$\gamma^{32}$P]ATP (Amersham) 0.3 μCi/reaction, ATP (Sigma) 9 μM/reaction, myelin basic protein (Sigma) 12 μg/reaction and MgCl2 50 mM/reaction. 4 μl phospholipids were added per reaction when needed. Phospholipids were prepared as described above. Kinase reactions were stopped with SDS sample buffer and boiling. Samples were then run on a 12% SDS PAGE and transferred to nitrocellulose exposed for autoradiography. The same nitrocellulose was then developed with anti εPKC (V5) antibodies (Santa Cruz Biotechnology) to verify the amount of fusion protein immunoprecipitated.

Analysis of PKC Translocation by Western Blot

After 24 hours of transfection cells were serum starved for an additional 24 hours and incubated with phorbol 12-myristate 13-acetate (PMA) (LC Laboratories) for the indicated times and concentrations at room temperature and subsequently fractionated as previously described [Schechtman, D & Mochly-Rosen, D., *Methods Enzymol.* 345:470-489 (2002)]. To assess PKC distribution the different cell fractions were run on SDS PAGE, transferred for Western blot analysis and probed with anti-εPKC V5 antibodies. Lysates of overexpressed GFP-εPKC were diluted to approximately 0.2 μg/well. At this concentration endogenous εPKC was not detected. All other methods for this Example were performed as described, for example, in Example 4.

Microscopy and Analysis

CHO cells were grown on glass coverslips, and serum-starved as described in Example 4. For each experiment, cells were transferred to a commercially available metal coverslip holder (Molecular Probes) in which the coverslip formed the bottom of a 1 ml bath. The media was then replaced with extracellular buffer (120 mM NaCl, 5 mM KCl, 1.5 mM CaCl2, 1.5 mM MgCl2, 20 mM HEPES and 30 mM glucose). Cells were stimulated by either PMA (100 nM), or with ATP (1 mM) in extracellular buffer. Fluorescence images of GFP-tagged constructs were obtained using the 488 nm excitation line of a laser scanning confocal microscope (Pascal, Zeiss) and emission was collected through a 505-550 nm band pass filter. Cells were imaged on the stage of an inverted microscope (Axiovert 100M) using a 40× Zeiss Plan-apo oil immersion objective with 1.2 numerical aperture (NA). For dual color imaging of CFP and YFP fusion proteins, a spinning disk Nipkow confocal microscope was used. Cells were viewed using an inverted Olympus IX70 microscope with a 40× oil immersion Olympus objective (1.35NA) and images were acquired with a CCD camera (Hamamatsu) and 2×2 pixel binning. CFP was excited with the 442 nm laser line of a helium-cadmium laser (Kimmon) whereas YFP was imaged with the 514 nm line of an argon ion laser (Melles-Griot). To selectively photobleach YFP labeled proteins in local regions of the cytoplasm for FRAP experiments, the 514 nm line of an Enterprise laser (Coherent) at maximal power (~400 mW) was used. For these experiments, a 60× oil immersion objective was used (1.4NA). Under these conditions, and by placing an iris in the beam path, it was possible to bleach 80% of the YFP fluorescence in 500 ms in an area of the cytosol measuring approximately 35 um2. Real time confocal images were acquired every 10-15 seconds for 20 minutes for experiments utilizing PMA, and every 5 seconds for a total duration of 3 minutes in the case of cells stimulated with ATP. Reagents were added to the cell chamber after the fifth image in each time series. Control time lapses were acquired using the same imaging conditions used in the experiments to check that the level of general dye photobleaching did not exceed 10-30%. All images were acquired at room temperature. Images were exported as 12 or 16 bit files and changes in fluorescence intensity were measured using MetaMorph® data analysis software (Universal Imaging Corp.). To monitor the translocation of PKC, a small region of interest was selected in the cytosol of each cell and fluorescence intensity values graphed against time after subtraction of background values and normalized so that the initial fluorescence was 100%. Averages of 10-15 cells from three independent experiments were used. To determine statistical significance, a 1 tail type 2 T-test (Microsoft excel) was used.

Immunoprecipitation

CHO-Hir cells were washed two times in serum free media and serum starved 12-24 hrs after transfection. Cells were then kept in serum free media for approximately 12 hours before the experiment. Cells were lysed in homogenization buffer [20 mM Tris-HCl, pH 7.5, 2 mM EDTA, 10 mM EGTA, 0.25M sucrose, 12 mM β-mercapthoethanol, PMSF (17 μg/ml), soybean trypsin inhibitor (SBTI), (20 μg/ml), leupeptin (25 μg/ml), aprotinin (25 μg/ml) and 0.1% Triton X100 (Sigma)] and centrifuged at 1000×g for 30 minutes. The supernatant was then used for immunoprecipitation experiments. Immunoprecipitation was performed with anti-GFP monoclonal antibodies 3E6 (Molecular Probes) according to the manufacturer's instruction. Briefly, lysates (approximately 2 mg/ml) were precleared in protein G agarose beads (25 μl packed volume Invitrogen) for at least 30 minutes and spun at 1000×g. The supernatant was then incubated with 1 μg anti-GFP monoclonal antibodies for at least two hours. Protein G agarose beads (25 μl packed volume) was then added to the lysate-antibodies complex and incubated for at least two hours (all incubations were done at 4° C.). Beads were subsequently washed three times with Buffer 1 (50 mM Tris, 0.15 M NaCl, 1 mM EDTA, 0.1% Triton X100, pH 7.5), once with Buffer 2 (50 mM Tris, 0.15 M NaCl, 0.1% Triton X100, pH 7.5) and once with Buffer 3 (50 mM Tris, 0.1% Triton X100, pH 7.5). For kinase assays, beads were washed an additional time with 20 mM Tris-HCl, pH 7.5.

Results

In an in vitro kinase assay, it was first confirmed that the GFP-fusion proteins had similar catalytic activity. As seen in FIGS. 6A and B, immunoprecipitated GFP-εPKC mutants phosphorylated myelin basic protein to a similar extent upon activation.

It was also confirmed that the Wt and ΨεRACK εPKC mutants were sensitive to activation by phorbol ester and that they translocated from the soluble to the particulate fraction of the cell upon activation. Translocation of the εPKC mutants was determined using two different cell lines, MCF-7 and CHO. [CHO cells were stimulated for 10 minutes with 100 nM PMA (FIG. 6C). MCF-7 cells were stimulated with 10 nM PMA for 10 minutes (FIG. 6D, 6E), since stimulation of MCF-7 cells with higher doses of PMA caused a detachment of the cells]. After treatment with PMA, cells were fractionated into soluble and particulate fractions, and GFP-εPKC was detected and quantified by Western blot analysis using anti-εPKC. Only GFP-εPKC fusion proteins (about 110 Kda) and not the endogenous εPKC (about 80 Kda) were detected when 20 ng of protein was loaded per lane and all the mutants had a similar level of expression (FIGS. 6C-6E). On PMA treatment, there was a greater increase in D(86)A εPKC in the particulate fraction than either D(86)N or Wt εPKCs (FIG. 6C, D). This is not due to PKC degradation; the total amount of εPKC was not changed upon activation. Therefore, GFP-εPKC ΨεRACK mutants were catalytically active and responded to activation by PMA by translocating from the soluble to the particulate fraction of the cell. Using two different cell lines, it was found that after 10 minutes of treatment with PMA, more D(86)A εPKC compared to Wt or D(86)N εPKCs translocated to the particulate fraction.

Since cell fractionation experiments are not suitable for dynamic studies, the GFP tag was used to follow the rate of translocation of the different εPKCs by real-time microscopy in CHO cells (FIGS. 7A-7C). Translocation of εPKC was seen as a decrease of fluorescence intensity in the cytoplasm concomitant with an increase in fluorescence intensity at the cell periphery. All of the εPKC mutants translocated to the same place (cell periphery) when stimulated by PMA (FIG. 7A). Translocation of the D(86)A mutant to the cell periphery began within one minute of PMA stimulation, whereas translocation of the Wt enzyme became apparent only after 2-3 minutes of PMA stimulation (FIG. 7A, arrows). In contrast, translocation of the D(86)N mutant became apparent only after 5 minutes of stimulation. A typical line intensity profile showing the distribution of each εPKC between the cell periphery and cytosol is shown for a representative cell at different time points (FIG. 7B).

The amount of fluorescence decrease in the cytoplasm was proportional to the amount of fluorescence increase at the cell periphery [Raghunath, A. et al. *Biochem. J.* 370:901-912 (2003)), since the total fluorescence did not change. To quantitatively monitor translocation of the different εPKC enzymes, the decrease of fluorescence intensity was measured in a region of the cytoplasm upon PMA stimulation using MetaMorph® software (Universal Imaging Corp.). A graphical comparison of εPKC translocation obtained by the decrease of fluorescence in the cytoplasm indicated that the rates of translocation were significantly different between the two mutants and Wt εPKC (p<0.0001; FIG. 7C). The D(86)A mutant translocated at a faster rate than either the Wt or D(86)N εPKC mutant. The Wt enzyme reaches a similar steady state level (the level at which there was no further accumulation of εPKC at the cell periphery) as the D(86)A mutant, but did so at a slower rate. In contrast, the D(86)N mutant achieved a steady state at a higher level than either the Wt or D(86)A mutant. Therefore, the D(86)A mutant translocated at a faster rate than either the D(86)N or Wt εPKCs, and the amount of D(86)N εPKC mutant that reached the cell periphery was lower than the amounts of either D(86)A or Wt εPKCs.

EXAMPLE 7

Mathematical Modeling of εPKC Translocation Suggests that εPKC Translocation is at Least a Two Step Process To further characterize the initial process of translocation of the different εPKC ΨεRACK mutants, the decrease of fluorescence in the cytoplasm was fitted to a mathematical model.

Mathematic Modeling

Mathematical modeling was obtained from data of cells expressing similar levels of the different εPKC ΨεRACK mutants. Non-linear least squares curve fitting analysis was performed using the EViews software (QMS) and differential equation analysis was performed using Berkeley Madonna™. All other methods for this Example were performed as described, for example, in Examples 4 and 6.

Fluorescence time courses were analyzed by a non-linear regression analysis with single and biexponential equations (1 and 2) as previously done by Nalefski and Newton Nalefski, E. A. & Newton, A. C., *Biochemistry* 40:13216-13229 (2001)], where I(t) is the concentration of observed molecules in the cytosol at time (t), and $C_{1-5}$ are constants.

$$I(t) = C_1 + C_2 e^{(-C_3(t))} \qquad 1.$$

$$I(t) = C_1 + C_2 e^{(-C_3(t))} + C_4 e^{(-C_5(t))} \qquad 2.$$

Residual error graphs obtained using single exponential equations (FIG. 8A) and using biexponential equations (FIG. 8B) for the D(86)A εPKC mutant translocation process is shown in FIGS. 8A-8D. Residual error analysis for D(86)N and Wt εPKCs showed similar results (data not shown). Since a superior fit, with a smaller and more equally distributed error was obtained with a bi-exponential equation, a two-step model was adopted to illustrate the initial process of εPKC translocation where the first step is the opening of εPKC and disruption of the intramolecular interaction between the ΨεRACK and the εRACK binding-site, and the second step is εPKC binding to the membrane (binding to the membrane in this case may be binding to either lipids or proteins). This process can be described as follows:

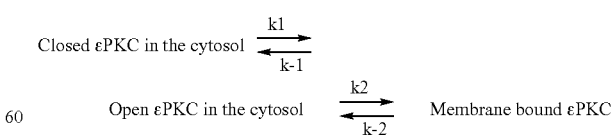

Where k1 is the rate of εPKC opening in the cytosol, k-1 is the rate of closing in the cytosol, k2 is the rate of εPKC binding to the membrane, and k-2 is the rate of detachment from the membrane. Using the bi-exponential equation, values for the constants C1, C3 and C5 (Table 1) were estimated.

Table I shows estimated constants using a bi-exponential equation and calculated values for k1, k-1, k2 and k-2

| εPKC | D(86)A | Wt | D(86)N |
|---|---|---|---|
| $C_1$ | 30.59 ± 0.286 | 30.46 ± 0.991 | 38.38 ± 0.254 |
| $C_3$ | 0.016 ± 0.001 | 0.016 ± 0.004 | 0.010 ± 0.0003 |
| $C_5$ | 0.040 ± 0.007 | 0.009 ± 0.001 | 0.034 ± 0.004 |
| k – 2/(k2 + k – 2) = $C_1$/100 | 0.306 ± 0.002 | 0.305 ± 0.010 | |
| (k2 + k – 2) = $C_3$ | 0.016 ± 0.001 | 0.016 ± 0.004 | |
| k – 2 | 0.005 ± 0.0004 | 0.005 ± 0.0011 | 0.0052 |
| k2 | 0.011 ± 0.003 | 0.011 ± 0.002 | 0.01138 |
| *k1 = $C_5$ | 0.040 ± 0.007 | 0.009 ± 0.001 | 0.0135 |
| k – 1 | ~0 | ~0 | 0.005 |

*For D(86)N the relations k1 = c5 is not valid since the corresponding values for k1, k – 1, k2 and k – 2 were obtained by simulations using differential equations.

The value of C1 corresponds to the level of εPKC in the cytosol at steady state. It was next determined whether the hypothesis that the values obtained for C1 and C3 of D(86)A and Wt εPKCs are statistically equivalent. Using WALD's parameter test, and using F-test and $\chi$i-Squared Test, p values of 0.9 and 0.7, respectively, were obtained. It was therefore assumed that the steady state level for A and D, C1, is the same. It was also assumed that the second step (binding to the membrane) should not differ between the εRACK εPKC mutants, since C3 was equal for both Wt and D(86)A εPKC. Therefore, if the steady state level (C1) was the same for D(86)A and Wt εPKCs and the second step (binding to the membrane) was also the same, it is plausible that k-1 (rate of closing of εPKC) for both D(86)A and D(86)N εPKCs would be negligible. When k-1 is negligible, the following equations (3-5) hold and can be used to calculate k-2 (equation 6) and K2 (Table 1).

$$(C1/100) = k-2/(k2+k-2) \quad 3.$$

$$C3 = (k2+k-2) \quad 4.$$

$$C5 = k1 \quad 5.$$

$$k-2 = [(C1/100)(C3)] \quad 6.$$

If $I_o(t)$ equals the concentration of closed εPKC in the cytosol at time (t), $I_1(t)$ equals the concentration of open εPKC in the cytosol at time (t), $I_2(t)$ equals the concentration of εPKC at the membrane at time (t) and I(t) equals the concentration of open and closed εPKC in the cytosol at time (t) ($I_o(t)+I_1(t)$), the following differential equations (7-9) can be used to describe this model:

$$dI_o(t)/dt = -(K1)(Io(t)) + (K-1)(I1(t)) \quad 7.$$

$$dI_1(t)/dt = -(K-1+K2)I_1(t) + (K1)(I_o(t)) + (K-2)(I_2(t)) \quad 8.$$

$$dI_2(t) = -(K-2)(I_2(t)) + (K2)(I_1(t)) \quad 9.$$

The differential equations were next solved for I(t) using the Runge-Kutta algorithm (Berkeley-Madonna) and the solutions were compared to the experimental data (loss of fluorescence in the cytoplasm). I(t) was solved for and the calculated parameters were used for k1, k-1, k2 and k-2 (Table 1) assuming that the initial amount of closed εPKC in the cytoplasm is equal to 100% [$I_o(0)$=100]. FIG. 8C shows the fit between curves of the raw data for D(86)A εPKC, and the curve obtained by nonlinear regression with a bi-exponential equation. FIG. 8D shows the fit between curves of the raw data for D(86)A and the curve obtained by the differential equations solving for I(t). Similar fitting results were obtained for D(86)N and Wt εPKCs (data not shown). The residual error for all curve fitting data was similar to the one obtained with a non-linear regression, using a bi-exponential equation (FIG. 4B; data not shown).

The steady state level for D(86)N was higher than for either D(86)A or Wt (Table 1), and therefore it is not possible to assume that k-1 for this mutant was negligible. In this case, the Runge-Kutta algorithm was also used to solve differential equations. Because the rate of the second step, binding to the membrane, should not be altered for either of the εPKC mutants, it was assumed that the values of k2 and k-2 should be in the range of the ones obtained for D(86)A and Wt. Together, the experimental data herein and mathematical modeling suggest a two-step translocation process of εPKC to the cell membrane upon activation. Whereas the second step was independent of intramolecular interactions, the first step, which was predicted herein to involve opening of the enzyme, was greatly dependent on these intramolecular interactions.

EXAMPLE 8

Co-Transfection of D(86)A ΨεRACK Mutant and Wt εPKC in the Same Cell

To further investigate the behavior of the εPKC mutants within a single cell, two different εPKC constructs were cotransfected into CHO cells, fused to either YFP or CFP. All methods for this Example were performed as described, for example, in Examples, 4, 6 and 7.

Results

A representative cell that co-expresses a YFP-A and a CFP-D εPKC at similar levels is shown in FIG. 9A. Upon stimulation with PMA, the D(86)A mutant translocated faster than the Wt enzyme (FIG. 9A). Quantitative analysis, expressing the decrease of fluorescence intensity in the cytoplasm is shown in FIG. 9C. The D(86)A mutant was found at the cell periphery at 1.5 minutes after PMA stimulation whereas translocation of Wt εPKC was still minimal even after 10 minutes (FIG. 9A). Therefore, even when the D(86)A ΨεRACK mutant and Wt εPKC were in the same cell, D(86)A translocated faster than Wt εPKC.

EXAMPLE 9

Translocation Rates of the ΨεRACK εPKC Mutants upon Cell Stimulation by a G Protein Coupled Receptor It was next determined whether differences in translocation rates of the different εPKCs were also observed when translocation was stimulated via receptor signaling rather than by PMA. ATP has been previously used to activate PKC in CHO cells by stimulating purinergic G protein-coupled receptors [Maasch, C. et al., *FASEB J.* 14:1653-1663 (2000)]. All methods for this Example were performed as described, for example, in Examples 4, 6 and 7.

Results

It was found herein that translocation of GFP-εPKC upon stimulation with ATP to the cell periphery was faster than PMA-induced translocation (FIG. 9B vs. FIGS. 7A-7C). Translocation of the D(86)A and Wt εPKCs was already apparent 10 seconds after stimulation, whereas translocation of the D(86)N εPKC enzyme occurred after 40 seconds of stimulation reaching a steady state at significantly higher levels than either D(86)A or Wt εPKCs (FIG. 9B). Quantitative analysis, expressing the decrease of fluorescence intensity in the cytoplasm is in FIG. 9D.

EXAMPLE 10

Diffusion Rates of the εPKC ΨεRACK Mutants

Different translocation rates may reflect differences in overall mobility (diffusion) of the εPKCs in cells. Therefore, fluorescence recovery after photobleaching (FRAP) of the cytoplasmic enzyme was measured; mobility of εPKCs was measured by monitoring the time required for the fluorescence to recover in a bleached region. All methods for this Example were performed as described, for example, in Examples 4, 6 and 7.

Fifty percent FRAP was reached at similar times for all εPKCs. (The average of at least 10 cells/each εPKC was: Wt=9.0±1.2, D(86)A=9.2±1.1 and D(86)N=9.1±1.6 seconds.) By comparing the fluorescence in the bleached region after full recovery (F∞) with that observed before bleaching (Fi) and just after bleaching (F0), the mobile fraction=(F∞−F0)/(Fi−F0) was determined. This was important to determine, since the mobile fraction may be affected by differences in interactions of the Wt and the mutant εPKCs with other proteins and membranes. It was found herein that the mobile fraction was the same for all εPKCs (63±2% for Wt, 63±4 for D(86)A and 64±2.5% for D(86)N, averages of at least 10 cells/each). Therefore, differences in translocation rates were not due to differences in mobility of the inactive enzyme, but rather, to modulation of the intramolecular interaction between the ΨεRACK and RACK-binding site.

Discussion

A key component in signal transduction is the inherent mechanism by which the enzymes remain inactive in the absence of extracellular stimuli. This mechanism involves the use of intramolecular interactions that stabilize a closed conformation with unexposed active site. Upon stimulation, the enzyme adopts an open conformation whereby intramolecular interactions are interrupted and binding sites for intermolecular interactions that stabilize the open form are exposed, resulting in a catalytically active enzyme. In the case of PKC, the intermolecular interaction sites are the binding sites for phospholipids and anchoring proteins [Mochly-Rosen, D & Gordon, A. S. *FASEB J.* 12:35-42 (1998); Oancea, E. et al., *J. Cell. Biol.* 140:485-498 (1998)]. Here, it is demonstrated that alterations in the intramolecular interaction between the εRACK binding site and the ΨεRACK site affected the translocation rate of the enzyme, further supporting a role of this intramolecular interaction in εPKC translocation and signaling.

As noted earlier, the ΨεRACK sequence in εPKC is about 25% different from the sequence in εRACK. It was suggested herein that the charge change (N-D) contributed to the difference in strength of the intramolecular interaction within εPKC as compared to the intermolecular interaction between εPKC and its RACK, εRACK [Souroujon, M. C. & Mochly-Rosen, D. Nat. Biotechnol. 16:919-924 (1998); Dorn, G. W. 2$^{nd}$, et al. *Proc. Natl. Acad. Sci. U.S.A.* 96:12798-12803 (1999)]. By mutating the D(86) in the ΨεRACK sequence of εPKC to an N, an enzyme that translocates slower than the wild type enzyme has been created, presumably because of the increase in the intramolecular interaction between the ΨεRACK and the RACK-binding site in εPKC. Mutating D(86) to an A in εPKC abolished the intramolecular interaction between the ΨεRACK and the RACK-binding site, and resulted in an enzyme that translocated at a faster rate than the wild type enzyme.

Mutations in the ΨεRACK Site in εPKC Affect Intrinsic Properties of εPKC

Three criteria were used to demonstrate the role of the ΨεRACK site in the intramolecular interaction within εPKC and the role of D86 in this interaction. The first criterion was the sensitivity of the enzyme to proteases; an open enzyme should be more susceptible to protease degradation after activation (Orr, J. W. et al., *J. Biol. Chem.* 267:15263-15266 (1992)]. It was shown herein that the D(86)N mutant was more resistant to proteolysis; D(86)N mutant required twice the time for the same extent of degradation of either the D(86)A or Wt enzymes (FIG. 5). Therefore, D(86)N mutant is a more closed or inactive enzyme. Because sensitivity to proteolysis of the A mutant was the same as wild type D(86) εPKC, it could not be determined whether it was conformationally different from the wild type enzyme using this method.

The second criterion examined PL-dependent binding of wild type and mutant enzymes to εRACK. If D(86) is critical for an intramolecular interaction, D(86)A should be less dependent on lipid activation for εRACK-binding. Indeed, the single amino-acid substitution modulated the intramolecular interaction between the ΨεRACK and the εRACK-binding site; the D(86)N mutant had a greater similarity to the εRACK sequence, and a reduced ability to bind to its εRACK, indicating that the D(86)N mutant is in a more closed conformation. In contrast, the D(86)A εPKC mutant was less dependent on activators for RACK binding, indicating that it is in a more open conformation.

Mutations in the ΨεRACK Site and Translocation Rates of εPKC in Cells

A third criterion demonstrating a critical role of the ΨεRACK site in intramolecular interactions examined the rate of translocation of the enzyme upon activation in cells. The D(86)A εPKC mutant translocated significantly faster than either D(86)N or Wt εPKCs, as measured by cell fractionation studies. Using real-time confocal microscopy it was demonstrated herein that the D(86)A mutant translocated at a faster rate than wild type εPKC, which in turn translocated faster than the D(86)N mutant. Together, it appears likely that the ΨεRACK site mediates a critical intramolecular interaction that stabilizes the closed conformation in εPKC in the absence of stimulation.

A scheme for the mechanism of translocation of the different εPKC mutants is shown in FIG. 10. Disruption of an intramolecular interaction between the ΨεRACK site and the εRACK-binding site must precede binding to the membrane and is a rate-limiting step in the process. Modulating this intramolecular interaction by mutating D(86) altered the translocation rates of εPKC, by affecting the first step of the translocation process. Mathematical modeling of the data herein further elucidated the molecular events leading to translocation (see FIG. 8). Using non-linear regression analysis, an equation with two exponents gave a better fit than a single exponential equation, indicating that PMA-induced translocation involves at least two steps (FIG. 7). It was proposed herein that the first step represents the opening and closing processes of the enzyme and the second step represents binding of the open enzyme to the cell membrane. Importantly, the steady state level of the D(86)N mutant was higher than that of either D(86)A or of Wt PKC, indicating that the amount of D(86)N that reached the cell periphery was lower than the amount of either Wt or D(86)A εPKCs. The D(86)A mutant translocated significantly faster than either the D(86)N or Wt εPKCs. Since the steady state level of D(86)A in the particulate fraction was similar to the steady state level of the Wt enzyme, and the second step of translocation (binding to the membrane) was the same for all mutants, the rate of closing of an enzyme, once it was open, could be considered negligible. Ochoa et al [*J. Mol. Bol.* 311:837-849 (2001)] demonstrated that the binding of the V1 domain to PL is not altered by D(86)A mutation, supporting the hypothesis proposed herein that the second step of translocation (binding to the membrane) is not altered [Ochoa et al [*J. Mol. Bol.* 311:837-849 (2001)]. However, for the N mutant, the k1 (rate of PKC opening) was slower than that of D(86)A and similar to Wt εPKC, and the k-1 (rate of εPKC closing) was no PKC longer negligible.

Similar to Shirai et al. [*J. Cell. Biol.* 143:511-521 (1998)], it was found herein that ATP-induced translocation of εPKC was much faster than PMA-induced translocation (FIG. 9B vs. 7). Since ATP-mediated translocation was a fast process, differences between the Wt and D(86)A mutants were not observed at the time intervals analyzed. However, the translocation of the D(86)N mutant was significantly slower than either the wild type or A mutant, further supporting the importance of the εRACK site and the disruption of intramolecular interaction for PKC translocation.

Schaefer et al., suggested that differences in translocation between classical and novel PKCs are due to differences in diffusion rates, and collision efficiencies with the membrane Schaefer, M. et al., *FASEB J.* 15:1634-1636 (2001; Lenz, J. C. et al., *J. Cell. Biol.* 159:291-302 (2002)]. Although diffusion and collision with the membrane are likely factors in the translocation rate, the data herein demonstrate that conformational changes in the enzyme also occur, leading to at least a two-step process.

In the case of the novel PKC (calcium-independent) isozymes, it is still not clear what triggers the opening of the enzyme. Here, it has been shown that disrupting the intramolecular interaction between the εRACK and RACK-binding site is a critical step in activation that precedes translocation and anchoring to the cell periphery. Whether this anchoring is mainly mediated by binding to membranes, whether it involves anchoring proteins, and whether binding to lipids precedes binding to proteins could not be determined in cells overexpressing εPKC. However, it has previously been demonstrated that translocation of endogenous εPKC results in its co-localization with its εRACK [Csukai, M. et al., *J. Biol. Chem.* 272:29200-29206 (1997)] and that disruption of binding to εRACK in cells with a peptide corresponding to one of the RACK-binding sites in εPKC (εV1-1 peptide) inhibits εPKC translocation and colocalization with εRACK [Johnson, J. A., et al., *J. Biol. Chem.* 271:24962-24966 (1996); Mochly-Rosen, D. et al., *Circ. Res.* 86:1173-1179 (2000)]. Importantly, it has been previously shown that a peptide corresponding to the ΨεRACK sequence induces εPKC translocation and co-localization with εRACK and triggers εPKC function [Dorn, G. W., 2$^{nd}$, et al:, *Proc. Natl. Acad. Sci. U.S.A.* 96:12798-12803 (1999)].

When the enzyme is over-expressed, as it is in this study, it is likely that the binding proteins including RACKs are no longer present in stochiometric amounts to the enzyme. Indeed, the over-expressed wild type εPKC and the endogenous εRACK did not co-localize in the cells, whereas the endogenous εPKC co-localized with the εRACK following activation in non-transfected cells (not shown). Because many attempts to co-express εRACK with εPKC have failed, the translocation experiments that performed in the present examples reflect mainly the interaction of the GFP-enzyme with lipids in the cell membrane.

Where in εPKC is this RACK-binding site? The V1 domain of εPKC is homologous to the C2 domain of the βPKC [Dekker, L. V., et al. *Curr. Opin. Struct. Biol.* 5:396-402 (1995)]. However, there is an additional RACK-binding site in the V5 region of βPKC (30) and molecular dynamics studies with the C2 region of βPKC showed that an intramolecular interaction between the ΨRACK and the RACK-binding site in the C2 region is not possible [Band, L. et al., *J. Biol. Chem.* 277:12988-12997 (2002)]. Instead it is suggested herein that the intramolecular interaction between the εRACK and the RACK-binding site in βPKC is likely to occur between the C2 and V5 regions in βPKC. This may also be the case for εPKC. Recently Stubbs and collaborators have demonstrated that in αPKC there is also an additional intramolecular interaction between the C1 and C2 domains that maintains the enzyme in its inactive state [Slater, S. J., et al., *J. Biol. Chem.* 277:15277-15285 (2002)]. In addition, they have suggested that αPKC forms dimers through an intermolecular interaction between the C1 and C2 domains. The hypothesis that this is also the case for the εRACK binding site and the ΨεRACK can not be rejected [Slater, S. J., et al., *J. Biol. Chem.* 277:15277-15285 (2002)].

By mutating the ΨεRACK site in the intact εPKC, it has been demonstrated herein the importance of interrupting the intramolecular interaction between the ΨεRACK and the εRACK-binding site in the process of εPKC translocation. To the inventor's knowledge, this is the first time that a single charge change made outside of the (Ψ-substrate) site or the catalytic site, or of calcium binding sites evoked a change in translocation rate. Together, it is concluded herein that disruption of the interaction between the ΨεRACK and the RACK-binding site is a critical and rate limiting step in PKC translocation.

From the foregoing, it can be seen how various objects and features of the invention are met. For example, a method for converting a PKC peptide agonist to a PKC peptide antagonist by changing an amino acid residue to effect a charge change in the agonist, such that, in one form of the invention, the modified agonist peptide more closely resembles the RACK, is described. The approach currently used to identify PKC isozyme-selective antagonists and agonists capitalizes on the availability of large databases containing the primary sequences of many proteins. Here, the approach was used to convert an isozyme specific translocation agonist to an antagonist by taking a peptide agonist, including ΨεRACK, and changing one amino acid residue (D to N). This change increased the peptide's resemblance to the RACK-derived sequence and also effected a charge change in the peptide. The change in activity of the modified peptide is illustrated in the Examples described herein by showing that regulation of cardiomyocyte contraction rate, an εPKC-mediated function that can be induced by ΨεRACK, was not induced by the peptide with an asparagine (N-ΨεRACK) or alanine (A-ΨεRACK) in the residue position of aspartate (D) in the ΨεRACK. Moreover, N-ΨεRACK inhibited PMA or ΨεRACK regulation of contraction as well as PMA- or ΨεRACK-induced εPKC translocation. Therefore, a single amino acid substitution, causing a change of charge, increased the resemblance of the peptide to the RACK sequence and resulted in loss of agonist activity and gain of antagonist activity.

Although the invention has been described with respect to particular embodiments, it will be apparent to those skilled in the art that various changes and modifications can be made without departing from the invention. Unless otherwise indicated, all terms herein have the same meaning as they would to one skilled in the art of the present invention. Practitioners are particularly directed to *Current Protocols in Molecular Biology* (Ausubel, F. M. et al., John Wiley and Sons, Inc., Media Pa.), which is regularly and periodically updated, for definitions and terms of the art.

What is claimed is:

1. A method of treating pain, comprising administering to a patient in need thereof a therapeutically effective amount of a composition comprising a first peptide comprising an amino acid sequence selected from the group consisting of SEQ ID NO:50, SEQ ID NO:51, SEQ ID NO:52, SEQ ID NO:53, SEQ ID NO:54, SEQ ID NO:55, SEQ ID NO:56, and SEQ ID NO:57, wherein said first peptide is crosslinked via a Cys-Cys bond to a second peptide to facilitate cellular uptake.

2. The method of claim 1, wherein said second peptide is selected from the group consisting of a Tat-derived peptide, an Antennapedia homeodomain-derived sequence, and a polyarginine peptide.

3. The method of claim 2, wherein said second peptide is a the Tat-derived peptide and wherein the Tat-derived peptide comprises SEQ ID NO:92.

4. The method of claim 2, wherein said second peptide is an Antennapedia homeodomain-derived sequence and the Antennapedia homeodomain-derived sequence comprises SEQ ID NO:91.

5. The method of claim 1, wherein said administering is by a route selected from the group consisting of intravenous, parenteral, and subcutaneous.

6. The method of claim 1, wherein said first peptide is crosslinked to said second peptide via an N-terminal Cys-Cys bond.

7. The method of claim 1, wherein said first peptide comprises SEQ ID NO:50.

8. The method of claim 1, wherein said first peptide comprises SEQ ID NO:51.

9. The method of claim 1, wherein said first peptide comprises SEQ ID NO:52.

10. The method of claim 1, wherein said first peptide comprises SEQ ID NO:53.

11. The method of claim 1, wherein said first peptide comprises SEQ ID NO:54.

12. The method of claim 1, wherein said first peptide comprises SEQ ID NO:55.

13. The method of claim 1, wherein said first peptide comprises SEQ ID NO:56.

14. The method of claim 1, wherein said first peptide comprises SEQ ID NO:57.

15. A method of treating pain, comprising administering to a patient in need thereof a therapeutically effective amount of a composition comprising a first peptide comprising the amino acid sequence of SEQ ID NO:55, wherein said first peptide is crosslinked via a Cys-Cys bond to a second peptide to facilitate cellular uptake, wherein said second peptide comprises the amino acid sequence of SEQ ID NO:92.

16. The method of claim 15, wherein said first peptide is crosslinked to said second peptide via an N-terminal Cys-Cys bond.

* * * * *